United States Patent [19]

Gehring et al.

[11] Patent Number: 4,936,892
[45] Date of Patent: Jun. 26, 1990

[54] 1-ARYLPYRAZOLES, COMPOSITIONS AND USE

[75] Inventors: Reinhold Gehring, Wuppertal; Otto Schallner, Monheim; Jörg Stetter, Wuppertal; Albrecht Marhold; Hans-Joachim Santel, both of Leverkusen; Robert R. Schmidt; Klaus Lürssen, both of Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 220,034

[22] Filed: Jul. 15, 1988

[30] Foreign Application Priority Data

Aug. 3, 1987 [DE] Fed. Rep. of Germany ....... 3725661

[51] Int. Cl.$^5$ .................. A01N 43/56; C07D 231/16
[52] U.S. Cl. .......................................... 71/74; 71/72; 71/92; 514/404; 514/407; 548/362; 548/376
[58] Field of Search .................. 548/362, 376; 71/72, 71/74, 92

[56] References Cited

U.S. PATENT DOCUMENTS

| 4,614,533 | 9/1986 | Schallner | 71/92 |
| 4,711,658 | 12/1987 | Gehring | 71/92 |
| 4,764,202 | 8/1988 | Gehring | 71/92 |
| 4,787,930 | 11/1988 | Gehring | 548/376 |
| 4,808,209 | 2/1989 | Gehring | 71/92 |

Primary Examiner—Robert W. Ramsuer
Attorney, Agent, or Firm—Sprung Horn Kramer & Woods

[57] ABSTRACT

A 1-arylpyrazole of the formula (I)

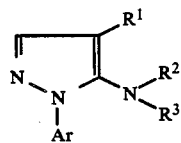

in which
R$^1$ stands for hydrogen or nitro,
R$^2$ stands for hydrogen, for a radical

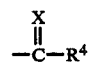

or a radical —S(O)$_n$—R$^5$,
R$^3$ stands for alkyl, for a radical $$-\overset{X}{\underset{\|}{C}}-R^4$$

or for a radical —S(O)$_n$—R$^5$, and, in addition, in the case where R$^2$ stands for a radical —SO$_2$—R$^5$, R$^3$ alternatively stands for an inorganic or organic cation bonded in the manner of a salt, where
R$^4$ stands for hydrogen, alkyl, alkenyl, alkinyl, monohalogenoalkyl, alkoxyalkyl, halogenoalkoxyalkyl, alkylthioalkyl, alkoxy, alkylthio, alkylsulphonylalkyl, alkylsulphinylalkyl, alkylamino, dialkylamino, optionally substituted cycloalkyl, optionally substituted aryl, optionally substituted aryloxy, optionally substituted arylthio, or for optionally substituted arylamino,
X stands for oxygen or sulphur,
R$^5$ stands for alkyl, halogenoalkyl or for optionally substituted aryl,
n stands for a number 0, 1 or 2, and
Ar stands for one of the radicals

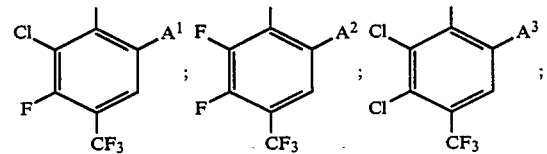

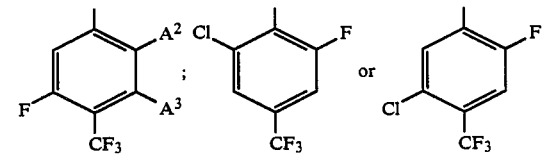

wherein
A$^1$ stands for hydrogen, fluorine or chlorine,
A$^2$ stands for fluorine or chlorine and
A$^3$ stands for hydrogen or fluorine, but excluding the compounds 5-ethoxycarbonylamino-1-(2,3-dichloro-4-trifluoromethylphenyl)-4-nitro- pyrazol and 5-acetamido-1-2,5-difluoro-4-trifluoromethylphenyl)-pyrazole. Such 1-arylpyrazoles are useful as herbicides and as plant growth-regulating agents.

14 Claims, No Drawings

1-ARYLPYRAZOLES, COMPOSITIONS AND USE

The invention relates to new 1-arylpyrazoles, several processes for their preparation, and their use as herbicides and plant growth regulators.

It has been disclosed that certain 1-arylpyrazoles, such as, for example, 5-chloroacetamido-1-(2,6-dichloro-4-trifluoromethylphenyl) -4-nitro-pyrazole, have herbicidal, in particular also selectively-herbicidal properties (cf. for example DE-OS (German Published Specification) No. 3,402,308).

The herbicidal activity of the disclosed compounds against harmful plants, and also their tolerance by important crop plants, are, however, not completely satisfactory in all areas of application.

New 1-arylpryrazoles of the general formula (I)

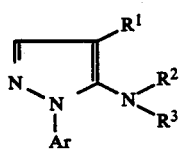

in which
R¹ stands for hydrogen or nitro,
R² stands for hydrogen, for a radical

or a radical —S(O)$_n$—R⁵,
R³ stands for alkyl, for a radical

or for a radical —S(O)$_n$—R⁵, and, in addition, in the case where R² stands for a radical —SO₂—R⁵
R³ alternatively stands for an inorganic or organic cation bonded in the manner of a salt,
where
R⁴ stands for hydrogen, alkyl, alkenyl, alkinyl, monohalogenoalkyl, alkoxyalkyl, halogenoalkoxyalkyl, alkylthioalkyl, alkoxy, alkylthio, alkylsulphonylalkyl, alkylsulphinylalkyl, alkylamino or dialkylamino, for optionally substituted cycloalkyl, for optionally substituted aryl, for optionally substituted aryloxy, for optionally substituted arylthio, or for optionally substituted arylamino,
X stands for oxgen or sulphur,
R⁵ stands for alkyl, halogenoalkyl or for optionally substituted aryl,
n stands for a number 0, 1 or 2, and
Ar stands for one of the radicals

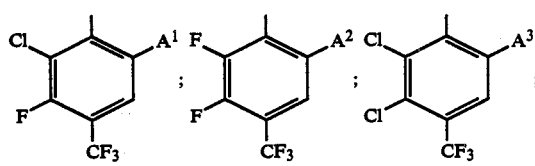

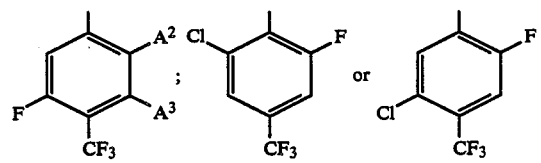

wherein
A¹ stands for hydrogen, fluorine or chlorine,
A² stands for fluorine or chlorine and
A³ stands for hydrogen or fluorine, but where the compounds 5-ethoxycarbonylamino-1-(2,3-dichloro-4-trifluoromethyphenyl)-4-nitro-pyrazole and 5-acetamido-1-(2,5-difluoro-4-trifluoromethylphenyl)-pyrazole, are excluded, have been found.

It has furthermore been found that the new 1-arylpyrazoles of the general formula (I)

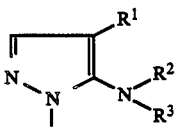

in which
R¹ stands for hydrogen or nitro,
R² stands for hydrogen, for a radical

or a radical —S(O)$_n$—R⁵,
R³ stands for alkyl, for a radical

or for a radical —S(O)$_n$—R⁵, and, in addition, in the case where R² stands for a radiccal —SO₂—R⁵, R³ alternatively stands for an inorganic or organic cation bonded in the manner of a salt,
where
R⁴ stands for hydrogen, alkyl, alkenyl and alkinyl, for monohalogenoalkyl, alkoxyalkyl, halogenoalkoxyalkyl, alkylthioalkyl, alkylsulphonylalkyl and alkylsulphinylalkyl, for optionally substituted cycloalkyl, for optionally substituted aryl, for alkoxy or alkythio, for optionally substituted aryloxy, for optionally substituted arylthio, for alkylamino or dialkylamino, or for optionally substituted arylamino,
X stands for oxygen or suplhur,
R⁵ stands for alkyl, halogenoalkyl or for optionally substituted aryl,
n stands for a number 0, 1 or 2, and
Ar stands for one of the radicals

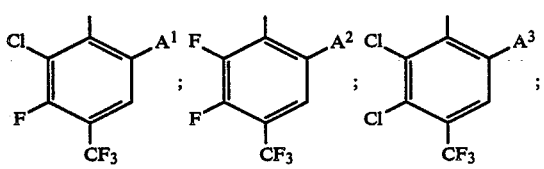

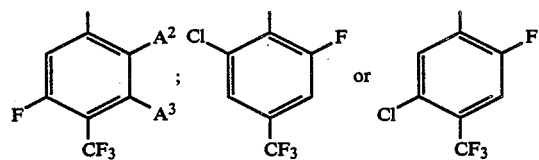

wherein
  $A^1$ stands for hydrogen, fluorine or chlorine,
  $A^2$ stands for fluorine or chlorine and
  $A^3$ stands for hydrogen or fluorine, but where the compounds 5-ethoxycarbonylamino-1-(2,3-dichloro-4-trifluoromethylphenyl)-4-nitropyrazole and 5-acetamido-1-(2,5-difluoro-4-trifluoromethylphenyl)-pyrazole are excluded,
can be prepared by the following processes:
  (a) 1-arylpyrazoles of the formula (Ia)

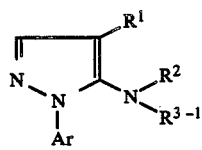

in which
  $R^{3-1}$ stands for alkyl, for a radical

or for a radical $-S(O)_n-R^5$ and
  $R^1, R^2, R^4, R^5, X, n$ and Ar have the abovementioned meanings,
are obtained when 1-arylpyrazoles of the formula (II)

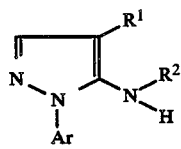

in which
  $R^1, R^2$ and Ar have the abovementioned meanings,
are reacted
(a—α) with acylating agents of the formula (III)

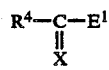

in which
  $E^1$ stands for an electron-withdrawing leaving group and
  $R^4$ and X have the abovementioned meanings, or
(a—β) with sulphenylating, sulphinylating or sulphonylating agents of the formula (IV)

$$R^5-S(O)_n-E^2 \qquad (IV)$$

in which
  $E^2$ stands for an electron-withdrawing leaving group and
  $R^5$ and n having the abovementioned meanings, or
(a—γ) with alkylating agents of the formula (V)

$$R^{3-2}-E^3 \qquad (V)$$

in which
  $R^{3-2}$ stands for alkyl and
  $E^3$ stands for an electron-withdrawing leaving group, in each case if appropriate in the presence of a diluent and also if appropriate in the presence of a reaction auxiliary;
  (b) 1-arylpyrazoles of the formula (Ib)

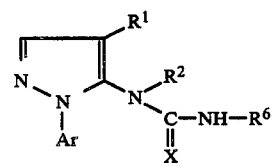

in which
  $R^6$ stands for alkyl or for optionally substituted aryl and
  $R^1, R^2, X$ and Ar have the abovementioned meanings,
are obtained when 1-arylpyrazoles of the formula (II)

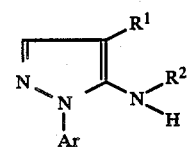

in which
  $R^1, R^2$ and Ar have the abovementioned meanings,
are reacted with iso(thio)cyanates of the formula (VI)

$$R^6-N=C=X \qquad (VI)$$

in which
  $R^6$ and X have the abovementioned meanings,
if appropriates in the presence of a diluent and if appropriate in the presence of a reaction auxiliary;
  (c) 1-arylpyrazoles of the formula (Ic)

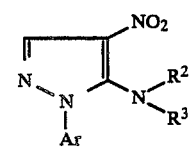

in which
  $R^2, R^3$ and Ar have the abovementioned meanings,
are obtained when 1-arylpyrazoles of the formula (Iz)

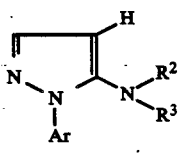
(Iz)

in which
R², R³ and Ar have the abovementioned meanings, are reacted with nitric acid, if appropriate in the presence of a diluent and if appropriate in the presence of a reaction auxiliary;

(d) 1-arylpyrazoles of the formula (Id)

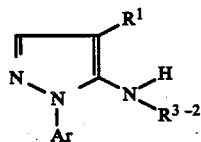
(Id)

in which
R³⁻² stands for alkyl and
R¹ and Ar have the abovementioned meanings,
are obtained when 1-arylpyrazoles of the formula (Iy)

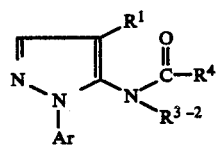
(Iy)

in which
R¹, R³⁻², R⁴ and Ar have the abovementioned meanings,
are hydrolyzed on the amino group in the 5-position of the pyrazole ring, if appropriate in the presence of a diluent and if appropriate in the presence of a reaction auxiliary;

(e) 1-arylpyrazoles of the formula (Ie)

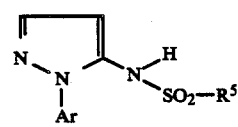
(Ie)

in which
R⁵ and Ar have the abovementioned meanings, are obtained when 1-arylpyrazoles of the formula (Ix)

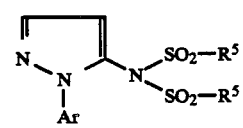
(Ix)

in which
R⁵ and Ar have the abovementioned meanings, are hydrolyzed on the amino group in the 5-position of the pyrazole ring, if appropriate in the presence of a diluent and if appropriate in the presence of a reaction auxiliary;

(f) 1-arylpyrazoles of the formula (If)

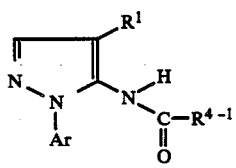
(If)

in which
R⁴⁻¹ stands for alkoxy, alkylthio, for optionally substituted aryloxy, for optionally substituted arylthio, for alkylamino or dialkylamino, or for optionally substituted arylamino, and
R¹ and Ar have the abovementioned meanings, are obtained when 1-arylpyrazoles of the formula (Iw)

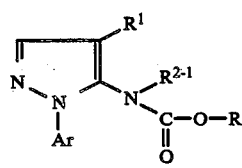
(Iw)

in which
R²⁻¹ stands for hydrogen or for a radical

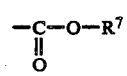

R⁷ stands for optionally substituted aryl and
R¹ and Ar have the abovementioned meanings,
are reacted with alcohols, amines or thiols of the formula (VII)

 (VII)

in which
R⁴⁻¹ has the abovementioned meaning, if appropriate in the presence of a diluent and if appropriate in the presence of a reaction auxiliary;

(g) 1-arylpyrazoles of the formula (Ig)

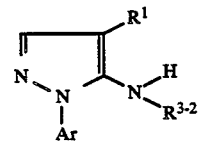
(Ig)

in which
R³⁻² stands for alkyl and
R¹ and Ar have the abovementioned meanings
are obtained when 5-halogeno-1-aryl-pyrazoles of the formula (VIII)

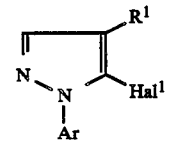
(VIII)

in which
Hal¹ stands for halogen and $R^1$ and Ar have the abovementioned meanings, are reacted with amines of the formula (IX)

$$H_2N—R^{3-2} \quad\quad\quad (IX)$$

in which
$R^{3-2}$ has the abovementioned meaning, if appropriate in the presence of a diluent and if appropriate in the presence of a reaction auxiliary;
(h) 1-arylpyrazoles of the formula (Ih)

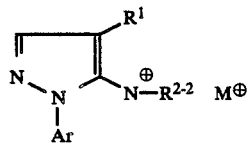

in which
$R^{2-2}$ stands for a radical $—SO_2—R^5$,
$M^\oplus$ stands for an equivalent of an inorganic or organic cation, and
$R^1$, $R^5$ and Ar have the abovementioned meanings,
are obtained when 1-arylpyrazoles of the formula (Iv)

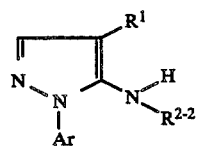

in which
$R^1$, $R^{2-2}$ and Ar have the abovementioned meanings, are reacted with salts of the formula (X)

$$M^\oplus—G^\ominus \quad\quad\quad (X)$$

in which
$M^\oplus$ has the abovementioned meaning and
$G^\ominus$ stands for an equivalent of a suitable counterion,
or with primary, secondary or tertiary amines, if appropriate in the presence of a diluent.

Finally, it has been found that the new 1-arylpyrazoles of the general formula (I) have herbicidal, in particular also selectively-herbicidal and plant growth-regulating properties.

Suprisingly, with equally good selectivity towards crop plants, the 1-arylpyrazoles of the general formula (I) according to the invention show a distinctly better herbicidal activity than the 1-arylpyrazoles known from the prior art such as, for example, 5-chloroacetamido-1-(2,6-dichloro-4-trifluoromethylphenyl)-4-nitropyrazole, which are chemically similar and have a similar action.

Formula (I) provides a general definition of the 1-arylpyrazoles according to the invention. Preferred compounds of the formula (I) are those
in which
$R^1$ stands for hydrogen or nitro,
$R^2$ stands for hydrogen, for a radical

or for a radical $—S(O)_n—R^5$,
$R^3$ stands for straight-chain or branched alkyl having 1 to 6 carbon atoms, for a radical

or for a radical $—S(O)_n—R^5$, and, in addition, in the case where $R^2$ stands for a radical $—SO_2—R^5$,
$R^3$ alternatively stands for an equivalent of an alkali metal cation or alkaline earth metal cation or transition metal cation bonded in the manner of a salt, or for an ammonium ion which is optionally substituted by $C_1-C_6$-alkyl or phenyl, where
$R^4$ stands for hydrogen, for straight-chain or branched alkyl having 1 to 12 carbon atoms, for alkenyl or alkynyl, in each case straight-chain or branched and in each case having 2 to 6 carbon atoms, for monohalogenoalkyl, alkoxyalkyl, halogenoalkoxyalkyl, alkylthioalkyl, alkoxy, alkylthio, alkylsulphonylalkyl, alkylsulphinylalkyl, alkylamino or dialkylamino, in each case straight-chain or branched and in each case having 1 to 4 carbon atoms in the individual alkyl moieties and, in the case of the halogenoalkoxyalkyl, having 1 to 9 identical or different halogen atoms, in addition for cycloalkyl which has 3 to 7 carbon atoms and is optionally monosubstituted or polysubstituted by identical or different substituents from the series comprising halogen and/or alkyl or halogenoalkyl, both straight-chain or branched and both having 1 to 4 carbon atoms and, in the case of the halogenoalkyl, having 1 to 9 identical or different halogen atoms, and also for phenyl, phenoxy, phenylthio or phenylamino, in each case optionally monosubstituted or polysubstituted by identical or different substituents, suitable phenyl substituents being in each case: halogen, alkyl or alkoxy, both straight-chain or branched and both having 1 to 4 carbon atoms, and also straight-chain or branched halogenoalkyl having 1 to 4 carbon atoms and 1 to 9 identical or different halogen atoms, X stands for oxygen or sulphur.
$R^5$ stands for alkyl or halogenoalkyl, in each case straight-chain or branched and in each case having 1 to 4 carbon atoms and where appropriate 1 to 9 identical or different halogen atoms, or for phenyl which is optionally monosubstituted or polysubstituted by identical or different substitutents, suitable phenyl substituents being: halogen, alkyl or alkoxy, both straight-chain or branched and both having 1 to 4 carbon atoms, and also straight-chain or branched halogenoalkyl having 1 to 4 carbon atoms and 1 to 9 identical or different halogen atoms,
n stands for a number 0, 1 or 2, and
Ar stands for one of the radicals

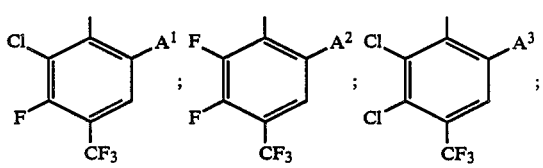

-continued

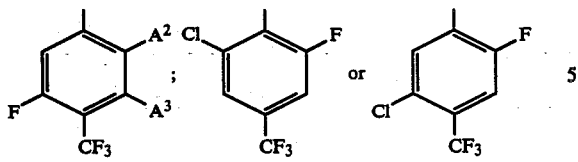

where
A¹ stands for hydrogen, fluorine or chlorine,
A² stands for fluorine or chlorine and
A³ stands for hydrogen or fluorine,
but where the compounds 5-ethoxycarbonylamino-1-(2,3-dichloro-4-trifluoromethylphenyl)-5-nitropyrazole and 5-acetamido-1-(2,5-difluoro-4-trifluoromethylphenyl)-pyrazole are excluded, Particularly preferred compounds of the formula (I) are those in which
$R^1$ stands for hydrogen or nitro,
$R^2$ stands for hydrogen, for a radical

or for a radical $-S(O)_n-R^5$,
$R^3$ stands for methyl, ethyl, n- or i-propyl, n-, i-, s- or t-butyl, for a radical

or for a radical $-S(O)_n-R^5$, and, in addition, in the case where $R^2$ stands for a radical $-SO_2-R^5$, $R^3$ alternatively stands for an equivalent of a sodium, potassium, magnesium, calcium, barium, copper, zinc, manganese, tin, iron, cobalt or nickel ion bonded in the manner of a salt, or for an ammonium ion which is optionally mono-substituted, disubstituted or trisubstituted by identical or different substituents from the series comprising methyl, ethyl, n- or i-propyl, n-, i-, s- or t-butyl or phenyl, wherein
$R^4$ stands for hydrogen, methyl, ethyl, n- or i-propyl, n-, i-, s- or t-butyl, for in each case straight-chain or branched pentyl, hexyl, heptyl, octyl, nonyl, decyl or undecyl, for vinyl, allyl, propargyl, n- or i-butenyl, methoxymethyl, ethoxymethyl, methoxyethyl, ethoxyethyl, n-propoxymethyl, isopropoxymethyl, methylthiomethyl, methoxy, ethoxy, methylthio, ethylthio, methylsulphonylmethyl, methylsulphonylethyl, ethylsulphonylmethyl, ethylsulphonylethyl, methylsulphinylmethyl, methylsulphinylethyl, ethylsulphinylmethyl, ethylsulphinylethyl, methylamino, ethylamino, dimethylamino, diethylamino, chloromethyl, iodomethyl, bromomethyl, 1-chloroethyl, 2-chloroethyl, 2-bromoethyl, 1-chloropropyl or 3-chloropropyl, for trifluoroethoxymethyl, for cyclopropyl, cyclopentyl or cyclohexyl, in each case optionally monosubstituted to tetrasubstituted by identical or different substituents from the series comprising fluorine, chlorine, bromine, methyl or trifluoromethyl, or for phenyl, phenoxy, phenylthio or phenylamino, in each case optionally monosubstituted, disubstituted or trisubstituted by identical or different substituents from the series comprising methyl, methoxy, chlorine or trifluoromethyl,
X stands for oxygen or sulphur,
$R^5$ stands for methyl, ethyl, n- or i-propyl, n-, i-, s- or t-butyl, chloromethyl, dichloromethyl, trichloromethyl or trifluoromethyl, or for phenyl which is optionally monosubstituted, disubstituted or trisubstituted by identical or different substituents from the series comprising methyl, methoxy, chlorine or trifluoromethyl,
n stands for a number 0, 1 or 2, and
Ar stands for one of the radicals

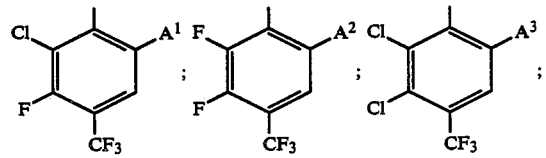

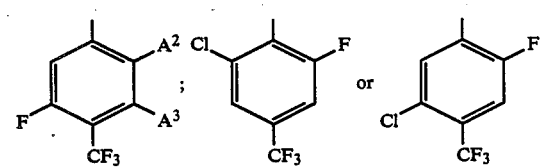

wherein
A¹ stands for hydrogen, fluorine or chlorine,
A² stands for fluorine or chlorine and
A³ stands for hydrogen or fluorine, but where the compounds 5-ethoxycarbonylamino-1-(2,3-dichloro-4-trifluoromethylphenyl)-4-nitropyrazole and 5-acetamido-1-(2,5-difluoro-4-trifluoromethylphenyl)-pyrazole are excluded.

Very particularly preferred compounds of the formula (I) are those
in which
$R^1$ stands for nitro,
$R^2$ stands for hydrogen,
$R^3$ stands for methyl, ethyl, n- or i-propyl, n-, i-, s- or t-butyl, for a radical

or for a radical $-SO_2-R^5$, where
$R^4$ stands for hydrogen, methyl, ethyl, n- or i-propyl, n-butyl, allyl, propargyl, n- or i-butenyl, for methoxymethyl, ethoxymethyl, n-propoxymethyl, isopropoxymethyl, methoxyethyl, ethoxyethyl, methylthiomethyl, methoxy, ethoxy, methylthio, ethylthio, methylamino, ethylamino, dimethylamino, diethylamino, chloromethyl, iodomethyl, bromomethyl, 1-chloroethyl, 2-chloroethyl, 2-bromoethyl, 1-chloropropyl or 3-chloropropyl, for trifluoroethoxymethyl, for cyclopropyl, cyclopentyl or cyclohexyl, or for phenyl, phenoxy, phenylthio or phenylamino, in each case optionally monosubstituted, disubstituted or trisubstituted by identical or different substituents from the series comprising methyl, methoxy, chlorine or trifluoromethyl,
$R^5$ stands for methyl, ethyl, n- or i-propyl, n-, i-, s- or t-butyl, chloromethyl, dichloromethyl, trichloromethyl or trifluoromethyl or for phenyl which is optionally monosubstituted, disubstituted or trisubstituted by identical or different substituents from the series comprising methyl, methoxy, chlorine or trifluoromethyl, and Ar stands for one of the radicals

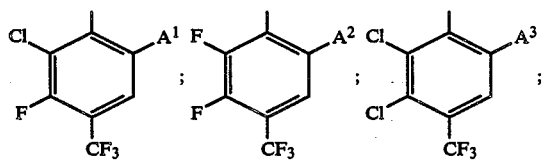

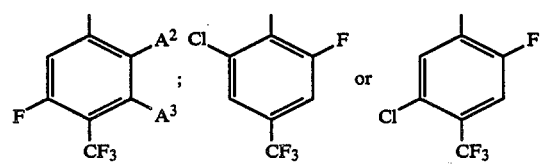

where
- $A^1$ stands for hydrogen, fluorine or chlorine,
- $A^2$ stands for fluorine or chlorine and
- $A^3$ stands for hydrogen of fluorine, but where the compounds 5-ethoxycarbonyl-amino-1-(2,3-dichloro-4-trifluoromethylphenyl)-4-nitropyrazole and 5-acetamido-1-(2,5-difluoro-4-trifluoromethylphenyl)-pyrazole are excluded.

Apart from the compounds mentioned in the preparation examples, the following 1-arylpyrazoles of the general formula (I)

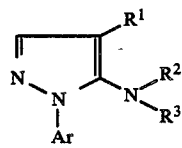 (I)

may be mentioned individually:

| $R^1$ | $R^2$ | $R^3$ | Ar |
|---|---|---|---|
| NO₂ | H | −C(=O)−CH₂−O−C₂H₅ | 2,6-Cl,Cl-4-CF₃-3-F-phenyl |
| NO₂ | H | −C(=O)−CH₂−O−CH(CH₃)₂ | 2,6-Cl,Cl-4-CF₃-3-F-phenyl |
| NO₂ | H | −C(=O)−CH₂−O−CH₂−CF₃ | 2,6-Cl,Cl-4-CF₃-3-F-phenyl |
| NO₂ | H | −C(=O)−CH₂−O−(CH₂)₂−CH₃ | 2,6-Cl,Cl-4-CF₃-3-F-phenyl |
| NO₂ | H | −C(=O)−CH₂Cl | 2,6-Cl,Cl-4-CF₃-3-F-phenyl |
| NO₂ | H | −C(=O)−CH(Cl)−C₂H₅ | 2,6-Cl,Cl-4-CF₃-3-F-phenyl |
| NO₂ | H | −C(=O)−N(CH₃)₂ | 2,6-Cl,Cl-4-CF₃-3-F-phenyl |
| NO₂ | H | −C(=O)−NH−C₂H₅ | 2,6-Cl,Cl-4-CF₃-3-F-phenyl |
| NO₂ | H | −SO₂−(CH₂)₃−CH₃ | 2,6-Cl,Cl-4-CF₃-3-F-phenyl |
| NO₂ | H | −C(=O)−O−C₂H₅ | 2,6-Cl,Cl-4-CF₃-3-F-phenyl |
| NO₂ | H | −C(=O)−O−C₆H₅ | 2,6-Cl,Cl-4-CF₃-3-F-phenyl |
| NO₂ | H | −C(=O)−NH−C₆H₅ | 2,6-Cl,Cl-4-CF₃-3-F-phenyl |

-continued

| R¹ | R² | R³ | Ar |
|---|---|---|---|
| NO₂ | H | −C(=O)−N(C₂H₅)₂ | 2,6-dichloro-3-fluoro-4-(CF₃)phenyl |
| NO₂ | H | −C(=O)−CH₂−OCH₃ | 2,6-dichloro-3-fluoro-4-(CF₃)phenyl |
| NO₂ | H | −C(=O)−CH₂−O−C₂H₅ | 2-chloro-6-fluoro-4-(CF₃)phenyl |
| NO₂ | H | −C(=O)−CH₂−O−CH(CH₃)₂ | 2-chloro-6-fluoro-4-(CF₃)phenyl |
| NO₂ | H | −C(=O)−CH₂−O−CH₂−CF₃ | 2-chloro-6-fluoro-4-(CF₃)phenyl |
| NO₂ | H | −C(=O)−CH₂−O−(CH₂)₂−CH₃ | 2-chloro-6-fluoro-4-(CF₃)phenyl |
| NO₂ | H | −C(=O)−CH₂Cl | 2-chloro-6-fluoro-4-(CF₃)phenyl |
| NO₂ | H | −C(=O)−CHCl−C₂H₅ | 2-chloro-6-fluoro-4-(CF₃)phenyl |
| NO₂ | H | −C(=O)−N(CH₃)₂ | 2-chloro-6-fluoro-4-(CF₃)phenyl |

-continued

| R¹ | R² | R³ | Ar |
|---|---|---|---|
| NO₂ | H | −C(=O)−NH−C₂H₅ | 2-chloro-6-fluoro-4-(CF₃)phenyl |
| NO₂ | H | −SO₂−(CH₂)₃−CH₃ | 2-chloro-6-fluoro-4-(CF₃)phenyl |
| NO₂ | H | −C(=O)−O−C₂H₅ | 2-chloro-6-fluoro-4-(CF₃)phenyl |
| NO₂ | H | −C(=O)−O−phenyl | 2-chloro-6-fluoro-4-(CF₃)phenyl |
| NO₂ | H | −C(=O)−NH−phenyl | 2-chloro-6-fluoro-4-(CF₃)phenyl |
| NO₂ | H | −C(=O)−N(C₂H₅)₂ | 2-chloro-6-fluoro-4-(CF₃)phenyl |
| NO₂ | H | −C(=O)−CH₂−OCH₃ | 2-chloro-6-fluoro-4-(CF₃)phenyl |
| NO₂ | H | −C(=O)−CH₂−O−C₂H₅ | 2,3-difluoro-6-chloro-4-(CF₃)phenyl |
| NO₂ | H | −C(=O)−CH₂−O−CH(CH₃)₂ | 2,3-difluoro-6-chloro-4-(CF₃)phenyl |

-continued

| R¹ | R² | R³ | Ar |
|---|---|---|---|
| NO₂ | H | —C(=O)—CH₂—O—CH₂—CF₃ | 2,3-difluoro-4-CF₃-6-Cl-phenyl |
| NO₂ | H | —C(=O)—CH₂—O—(CH₂)₂—CH₃ | 2,3-difluoro-4-CF₃-6-Cl-phenyl |
| NO₂ | H | —C(=O)—CH₂Cl | 2,3-difluoro-4-CF₃-6-Cl-phenyl |
| NO₂ | H | —C(=O)—CH(Cl)—C₂H₅ | 2,3-difluoro-4-CF₃-6-Cl-phenyl |
| NO₂ | H | —C(=O)—CH(Cl)—CH₃ | 2,3-difluoro-4-CF₃-6-Cl-phenyl |
| NO₂ | H | —C(=O)—N(CH₃)₂ | 2,3-difluoro-4-CF₃-6-Cl-phenyl |
| NO₂ | H | —C(=O)—OCH₃ | 2,3-difluoro-4-CF₃-6-Cl-phenyl |
| NO₂ | H | —C(=O)—NH—C₂H₅ | 2,3-difluoro-4-CF₃-6-Cl-phenyl |
| NO₂ | H | —C(=O)—O—C₂H₅ | 2,3-difluoro-4-CF₃-6-Cl-phenyl |

-continued

| R¹ | R² | R³ | Ar |
|---|---|---|---|
| NO₂ | H | —SO₂—CH₃ | 2,3-difluoro-4-CF₃-6-Cl-phenyl |
| NO₂ | H | —C(=O)—O—C₆H₅ | 2,3-difluoro-4-CF₃-6-Cl-phenyl |
| NO₂ | H | —C(=O)—NH—C₆H₅ | 2,3-difluoro-4-CF₃-6-Cl-phenyl |
| NO₂ | H | —C(=O)—N(C₂H₅)₂ | 2,3-difluoro-4-CF₃-6-Cl-phenyl |
| NO₂ | H | —C(=O)—CH₂—OCH₃ | 2,3-difluoro-4-CF₃-6-Cl-phenyl |
| NO₂ | H | —C(=O)—CH₂—O—C₂H₅ | 2-Cl-3-F-4-CF₃-phenyl |
| NO₂ | H | —C(=O)—CH₂—O—CH(CH₃)₂ | 2-Cl-3-F-4-CF₃-phenyl |
| NO₂ | H | —C(=O)—CH₂—O—CH₂—CF₃ | 2-Cl-3-F-4-CF₃-phenyl |
| NO₂ | H | —C(=O)—CH₂—O—(CH₂)₂—CH₃ | 2-Cl-3-F-4-CF₃-phenyl |
| NO₂ | H | —C(=O)—CH₂Cl | 2-Cl-3-F-4-CF₃-phenyl |

-continued

| R¹ | R² | R³ | Ar |
|---|---|---|---|
| NO₂ | H | −C(=O)−CH(Cl)−CH₃ | 3-Cl, 2-F, 4-CF₃ phenyl |
| NO₂ | H | −C(=O)−CH(Cl)−C₂H₅ | 3-Cl, 2-F, 4-CF₃ phenyl |
| NO₂ | H | −C(=O)−N(CH₃)₂ | 3-Cl, 2-F, 4-CF₃ phenyl |
| NO₂ | H | −C(=O)−NH−C₂H₅ | 3-Cl, 2-F, 4-CF₃ phenyl |
| NO₂ | H | −SO₂−CH₃ | 3-Cl, 2-F, 4-CF₃ phenyl |
| NO₂ | H | −C(=O)−O−C₂H₅ | 3-Cl, 2-F, 4-CF₃ phenyl |
| NO₂ | H | −C(=O)−OCH₃ | 3-Cl, 2-F, 4-CF₃ phenyl |
| NO₂ | H | −C(=O)−O−C₆H₅ | 3-Cl, 2-F, 4-CF₃ phenyl |
| NO₂ | H | −C(=O)−NH−C₆H₅ | 3-Cl, 2-F, 4-CF₃ phenyl |
| NO₂ | H | −C(=O)−N(C₂H₅)₂ | 3-Cl, 2-F, 4-CF₃ phenyl |
| NO₂ | H | −C(=O)−CH₂−OCH₃ | 3-Cl, 2-F, 4-CF₃ phenyl |
| NO₂ | H | −C(=O)−CH₂−O−C₂H₅ | 2,3-di-Cl, 4-CF₃ phenyl |
| NO₂ | H | −C(=O)−CH₂−O−CH(CH₃)₂ | 2,3-di-Cl, 4-CF₃ phenyl |
| NO₂ | H | −C(=O)−CH₂−O−CH₂−CF₃ | 2,3-di-Cl, 4-CF₃ phenyl |
| NO₂ | H | −C(=O)−CH₂−O−(CH₂)₂−CH₃ | 2,3-di-Cl, 4-CF₃ phenyl |
| NO₂ | H | −C(=O)−CH₂Cl | 2,3-di-Cl, 4-CF₃ phenyl |
| NO₂ | H | −C(=O)−CH(Cl)−CH₃ | 2,3-di-Cl, 4-CF₃ phenyl |
| NO₂ | H | −C(=O)−CH(Cl)−C₂H₅ | 2,3-di-Cl, 4-CF₃ phenyl |
| NO₂ | H | −C(=O)−N(CH₃)₂ | 2,3-di-Cl, 4-CF₃ phenyl |
| NO₂ | H | −C(=O)−NH−C₂H₅ | 2,3-di-Cl, 4-CF₃ phenyl |
| NO₂ | H | −SO₂−CH₃ | 2,3-di-Cl, 4-CF₃ phenyl |
| NO₂ | H | −C(=O)−O−CH₃ | 2,3-di-Cl, 4-CF₃ phenyl |

-continued

| R¹ | R² | R³ | Ar |
|---|---|---|---|
| NO₂ | H | -C(=O)-O-C₆H₅ (phenyl ester) | 2,3-diCl-4-CF₃-phenyl |
| NO₂ | H | -C(=O)-NH-C₆H₅ | 2,3-diCl-4-CF₃-phenyl |
| NO₂ | H | -C(=O)-N(C₂H₅)₂ | 2,3-diCl-4-CF₃-phenyl |
| NO₂ | H | -C(=O)-CH₂-OCH₃ | 2,3-diCl-4-CF₃-phenyl |
| NO₂ | H | -C(=O)-CH₂-O-C₂H₅ | 2-Cl-3-F-4-CF₃-5-F-phenyl |
| NO₂ | H | -C(=O)-CH₂-O-CH(CH₃)₂ | 2-Cl-3-F-4-CF₃-5-F-phenyl |
| NO₂ | H | -C(=O)-CH₂-O-CH₂-CF₃ | 2-Cl-3-F-4-CF₃-5-F-phenyl |
| NO₂ | H | -C(=O)-CH₂-O-(CH₂)₂-CH₃ | 2-Cl-3-F-4-CF₃-5-F-phenyl |
| NO₂ | H | -C(=O)-CH₂Cl | 2-Cl-3-F-4-CF₃-5-F-phenyl |
| NO₂ | H | -C(=O)-CH(Cl)-CH₃ | 2-Cl-3-F-4-CF₃-5-F-phenyl |
| NO₂ | H | -C(=O)-CH(Cl)-C₂H₅ | 2-Cl-3-F-4-CF₃-5-F-phenyl |
| NO₂ | H | -C(=O)-N(CH₃)₂ | 2-Cl-3-F-4-CF₃-5-F-phenyl |
| NO₂ | H | -C(=O)-NH-C₂H₅ | 2-Cl-3-F-4-CF₃-5-F-phenyl |
| NO₂ | H | -SO₂-CH₃ | 2-Cl-3-F-4-CF₃-5-F-phenyl |
| NO₂ | H | -C(=O)-O-C₂H₅ | 2-Cl-3-F-4-CF₃-5-F-phenyl |
| NO₂ | H | -C(=O)-O-CH₃ | 2-Cl-3-F-4-CF₃-5-F-phenyl |
| NO₂ | H | -C(=O)-O-C₆H₅ | 2-Cl-3-F-4-CF₃-5-F-phenyl |
| NO₂ | H | -C(=O)-NH-C₆H₅ | 2-Cl-3-F-4-CF₃-5-F-phenyl |

-continued

| R¹ | R² | R³ | Ar |
|---|---|---|---|
| NO₂ | H | −C(=O)−N(C₂H₅)₂ | 2-Cl-3-F-4-CF₃-6-F-phenyl |
| NO₂ | H | −C(=O)−CH₂−OCH₃ | 2-Cl-3-F-4-CF₃-6-F-phenyl |
| NO₂ | H | −C(=O)−CH₂−O−C₂H₅ | 2,3-F₂-4-CF₃-6-F-phenyl |
| NO₂ | H | −C(=O)−CH₂−O−CH(CH₃)₂ | 2,3-F₂-4-CF₃-6-F-phenyl |
| NO₂ | H | −C(=O)−CH₂−O−CH₂−CF₃ | 2,3-F₂-4-CF₃-6-F-phenyl |
| NO₂ | H | −C(=O)−CH₂−O−(CH₂)₂−CH₃ | 2,3-F₂-4-CF₃-6-F-phenyl |
| NO₂ | H | −C(=O)−CH₂Cl | 2,3-F₂-4-CF₃-6-F-phenyl |
| NO₂ | H | −C(=O)−CH(Cl)−CH₃ | 2,3-F₂-4-CF₃-6-F-phenyl |
| NO₂ | H | −C(=O)−CH(Cl)−C₂H₅ | 2,3-F₂-4-CF₃-6-F-phenyl |
| NO₂ | H | −C(=O)−N(CH₃)₂ | 2,3-F₂-4-CF₃-6-F-phenyl |
| NO₂ | H | −C(=O)−NH−C₂H₅ | 2,3-F₂-4-CF₃-6-F-phenyl |
| NO₂ | H | −SO₂−CH₃ | 2,3-F₂-4-CF₃-6-F-phenyl |
| NO₂ | H | −C(=O)−O−C₂H₅ | 2,3-F₂-4-CF₃-6-F-phenyl |
| NO₂ | H | −C(=O)−O−CH₃ | 2,3-F₂-4-CF₃-6-F-phenyl |
| NO₂ | H | −C(=O)−O−phenyl | 2,3-F₂-4-CF₃-6-F-phenyl |
| NO₂ | H | −C(=O)−NH−phenyl | 2,3-F₂-4-CF₃-6-F-phenyl |
| NO₂ | H | −C(=O)−N(C₂H₅)₂ | 2,3-F₂-4-CF₃-6-F-phenyl |

| R¹ | R² | R³ | Ar |
|---|---|---|---|
| NO₂ | H | —C(=O)—CH₂—OCH₃ | 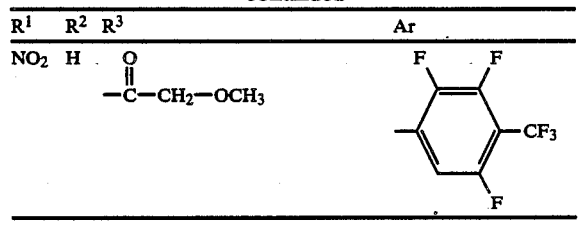 |

If, for example, 5-amino-1-(2-chloro-6-fluoro-4-trifluoromethylphenyl)-pyrazole and acetic anhydride are used as starting substances, the course of the reaction of process (a—α) according to the invention can be represented by the following equation:

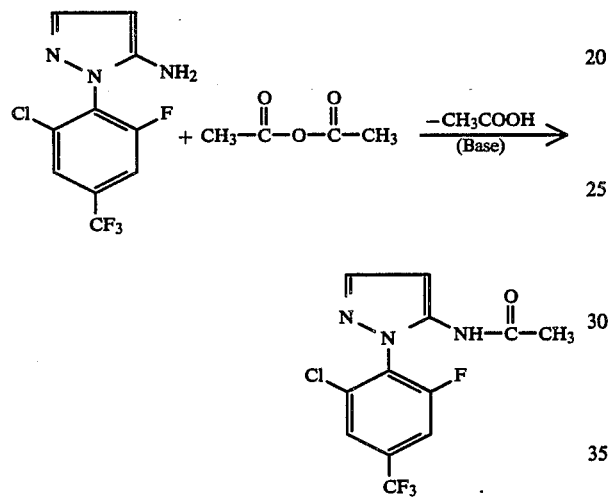

If, for example, 5-amino-1-(2,6-dichloro-3-fluoro-4-trifluoromethylphenyl)-pyrazole and methanesulphonyl chloride are used as starting substances, the course of the reaction of process (a—α) according to the invention can be represented by the following equation:

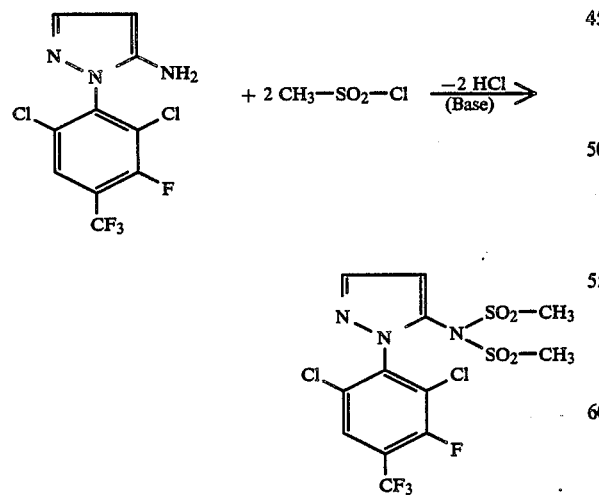

If, for example, 4-nitro-5-acetamido-1-(2,3-dichloro-4-trifluoromethylphenyl)-pyrazole and dimethyl sulphate are used as starting substances, the course of the reaction of process (a=γ) according to the invention can be represented by the following equation:

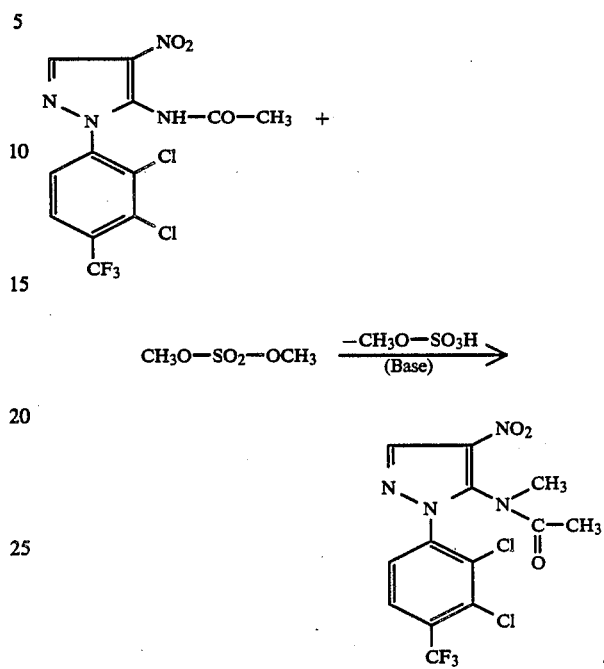

If, for example, 5-amino-4-nitro-1-(2,3,5-trifluoro-4-trifluoromethylphenyl)-pyrazole and phenyl isocyanate are used as starting substances, the course of the reaction of process (b) according to the invention can be represented by the following equation:

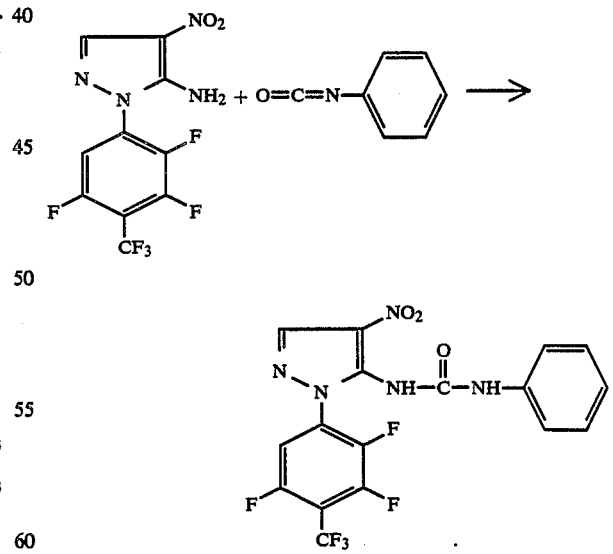

If, for example, 5-acetamido-1-(2-chloro-6-fluoro-4-trifluoromethylphenyl)-pyrazole and nitric acid are used as starting substances, the course of the reaction of process (c) according to the invention can be represented by the following equation:

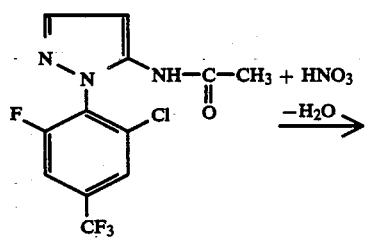

+ HNO₃ $\xrightarrow{-H_2O}$

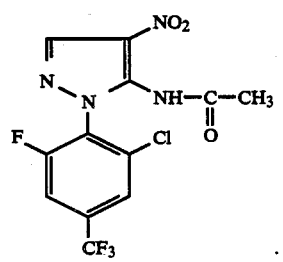

If, for example, 5-(N-ethyl-N-propionylamino)-4-nitro-1-(2-chloro-3,5-difluoro-4-trifluoromethylphenyl)-pyrazole is used as the starting compound, the course of the reaction of process (d) according to the invention can be represented by the following equation:

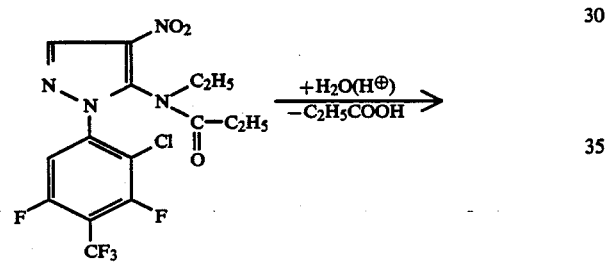

If, for example, 5-[N,N-bis-(methylsulphonyl)-amino]-1-(2-chloro-3-fluoro-4-trifluoromethylphenyl)-pyrazole and ammonia are used as starting substances, the course of the reaction of process (e) according to the invention can be represented by the following equation:

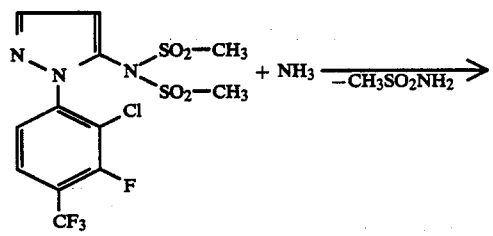

+ NH₃ $\xrightarrow{-CH_3SO_2NH_2}$

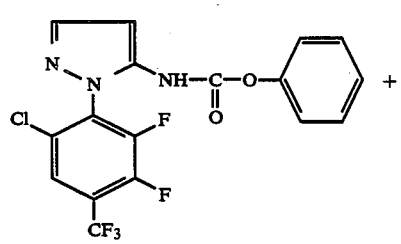

If, for example, 5-phenoxycarbonylamino-1-(2,3-difluoro-6-chloro-4-trifluoromethylphenyl)-pyrazole and methanol are used as starting substances, the course of the reaction of process (f) according to the invention can be represented by the following equation:

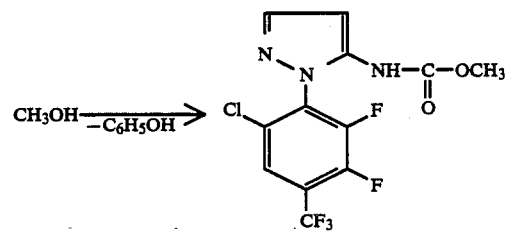

CH₃OH $\xrightarrow{-C_6H_5OH}$

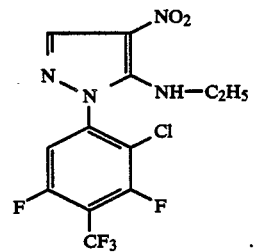

If, for example, 5-bromo-4-nitro-1-(2,6-dichloro-3-fluoro-4-trifluoromethylphenyl)-pyrazole and isopropylamine are used as starting substances, the course of the reaction of process (g) according to the invention can be represented by the following equation:

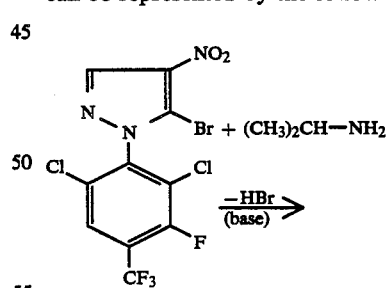

$\xrightarrow[\text{(base)}]{-HBr}$

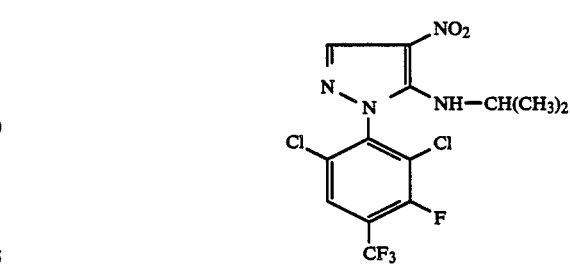

If, for example, 4-nitro-5-methanesulphonamido-1-(2-chloro-6-fluoro-4-trifluoromethylphenyl)-pyrazole and sodium bicarbonate are used as starting substances, the course of the reaction of process (h) according to the invention can be represented by the following equation:

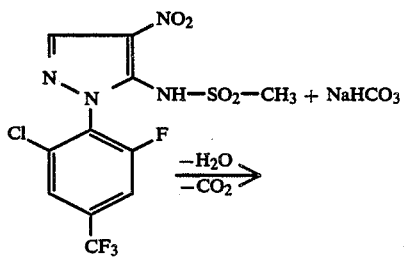

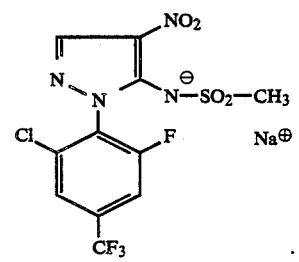

Formula (II) provides a general definition of the 1-arylpyrazoles required as starting substances for carrying out processes (a) and (b) according to the invention. In this formula (II), $R^1$, $R^2$ and Ar preferably stand for those radicals which have already been mentioned in connection with the description of the substances of the formula (I) according to the invention as being preferred for these substituents.

The 1-aryl-pyrazoles of the formula (II) were hitherto unknown.

1-Arylpyrazoles of the formula (II) in which $R^2$ stands for a radical

or for a radical $-S(O)_n-R^5$ where $R_4$, $R^5$, X and n have the abovementioned meaning, are compounds according to the invention and can be obtained with the aid of processes (a—α), (a—β), (b), (c), (e) or (f) according to the invention.

1-Arylpyrazoles of the formula (II) in which $R^2$ stands for hydrogen are the subject of a German patent application by the Applicant Company(cf. German Patent Application OS No. 3,617,977, publisched Jun. 11, 1987).

They are obtained when aryl halides of the formula (XI)

in which

Hal$^2$ stands for halogen, in particular for chlorine or fluorine and

Ar has the abovementioned meaning, are reacted initially in a first step with hyrazine hydrate, if appropriate in the presence of a diluent, such as, for example, ethanol or pyridine, at temperatures between 20° C. and 120° C.; the aryl hydrazines of the formula (XII)

in which

Ar has the abovementioned meaning, obtainable in this way are then reacted in a 2nd step with alkoxymethylenenitrilomalonates of the formula (XIII)

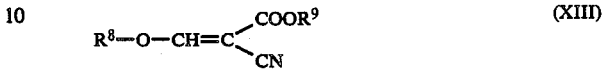

in which $R^8$ and $R^9$ independently of one another each stand for alkyl, in particular for methyl or ethyl, if appropriate in the presence of a diluent such as, for example, ethanol, at temperatures between 20° C. and 120° C.; the 1-arylpyrazole-4-carboxylates of the formula (XIV)

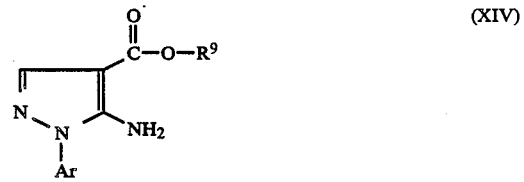

in which $R^9$ and Ar have the abovementioned meanings, obtainable in this way are then hydrolyzed and decarboxylated in a 3rd step using acids such as, for example, aqueous sulphuric acid, at temperatures between 80° C. and 150° C., and the 1-aryl-5-amino-pyrazoles of the formula (IIa)

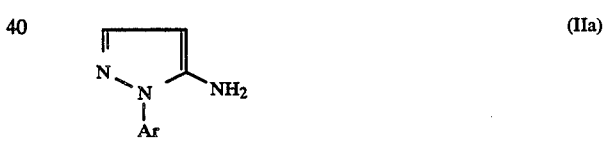

in which

Ar has the abovementioned meaning, obtainable in this way are, if appropriate, nitrated in a 4th step using a nitrating agent such as, for example, nitric acid, if appropriate in the presence of a diulent such as, for example, glacial acetic acid and, if appropriate, in the presence of a reaction auxiliary such as, for example, acetic anhydride, in analogy to the method of carrying out process (c) according to the invention, at temperatures between −20° C. and +50° C.

When carrying out this process, it may in some cases, be advantageous to protect the amino group in the 5-position of the pyrazole ring, before the nitrating reaction takes place, with the aid of customary techniques using protective groups, for example by acylation, and, after the nitration has been completed, to eliminate the amino protective group likewise in a customary fashion, for example by hydrolysis using aqueous or alcoholic bases.

Alternatively, 1-aryl-5-aminopyrazoles of the formula (IIa)

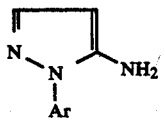 (IIa)

in which
Ar has the abovementioned meaning, are also obtained when arylhydrazines of the formula (XII)

 (XII)

in which
Ar has the abovementioned meaning,
are reacted with 2-halogenoacrylonitrile derivatives of the formula (XV)

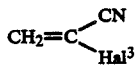 (XV)

in which
Hal³ stands for halogen, in particular for chlorine or bromine,
if appropriate in the presence of a diluent such as, for example, ethanol, and if appropriate in the presence of a reaction auxiliary such as, for example, sulphuric acid or trifluoroacetic acid, at temperatures between 50° C. and 150° C.

Most of the aryl halides of the formula (XI) are new and form the subject-matter of an application filed in parallel (cf. German Patent Application P No. 37 25 659.9, filed Aug. 3, 1987). They are obtained in analogy to processes which have been disclosed (cf., the example, European Patent Specification No. 187,023; European Patent Specification No. 180,057; U.S. Pat. No. 4,388,472; Zh. Org. Khim., 20, 2187-2191 [1984] or CA,102: 112944s; J. Fluorine Chem., 4, 317-326 [1974]; J. Chem. Soc. C, 1969, 211-217).

Furthermore, in the abovementioned application filed in parallel, a non-obvious process is described for the preparation of benzotrifluorides of the formula (XI) which are by fluorine and, if appropriate, additionally substituted by chlorine, in which benzotrifluorides containing fluorine and chlorine are hydrogenated in the presence of a catalyst and a hydrogen chloride acceptor (cf. the Preparation Examples XI-3 to XI-7).

Suitable catalysts are hydrogenating catalysts which are known in principle, for example, those containing the elements of subgroup VIII of the Periodic Table in their metallic form or in the form of compounds. Particularly suitable are nickel, platinum, palladium and compounds thereof, for example in the form of Raney nickel, metallic platinum, metallic palladium and palladium tetra (triphenylphoshine). The catalytically active substance may also be coated onto support materials, for example activated charcoal, silica, alumina, silicates or alkaline earth metal sulphates.

Preferred catalysts are Raney nickel and metallic palladium on activated charcoal.

The catalysts may alternatively be composed of several components, and, for example, can also contain promoters, suitable promoters also being element and compounds other than those of the metals of subgroup VIII of the Periodic Table.

In general, the quantity of catalyst is not critical. For example, it may be 0.01 to 15% by weight relative to the active catalyst. Preferably, this quantity is 0.1 to 10% by weight relative to the active catalyst (i.e., for example, to Pd coated onto activated charcoal.)

In general, the hydrogenation is carried out in the presence of solvents or diluents. It is not absolutely necessary for these to be able to dissolve the materials employed completely, as it is also possible for a two-phase substrate to be hydrogenated. For example, the initial benzotrifluoride and/or the hydrogen chloride acceptor may be present in completely or partly suspended form during the hydrogenation. Suitable solvents and diluents are, for example, organic acids, such as acetic acid; alcohols, such as methanol, ethanol, propanol and isopropanol; ethers, such as tetrahydrofuran; nitriles, such as acetonitrile, and also water.

Suitable hydrogen chloride acceptors are a very wide variety of inorganic and organic bases, for example hydroxides, carbonates, acetates and ammonium salts of the alkali metals and alkaline earth metals, and amines, in particular tertiary amines. Sodium acetate, triethylamine, N,N-dimethylaniline, pyrimidine and picoline are preferred.

The hydrogen chloride acceptor can be employed in various quantities. Preferably, at least 0.8 equivalents of hydrogen chloride acceptor are employed per equivalent of chlorine atoms to be eliminated from the benzotrifluoride employed. If all chlorine atoms present are to be eliminated from the benzotrifluoride employed, the upper limit of the quantity of the hydrogen chloride acceptor to be employed is not critical. For practical reasons it is generally advantageous in this case to employ not more than 2 equivalents of hydrogen chloride acceptor per equivalent of chlorine atoms to be eliminated. If not all chlorine atoms present are to be eliminated from the benzotrifluoride employed, i.e., benzotrifluorides still containing chlorine atoms are to be prepared, then the hydrogen chloride acceptor must not be employed in quantities which are considerably higher than stoichiometrically required. Preferably, in this case, up to 1.2, particularly preferably up to 1.05 and very particularly preferably 1 equivalent of hydrogen chloride acceptor is employed per equivalent of chlorine atoms to be eliminated.

The hydrogenation can, for example, be carried out in pressure ranges from atmospheric pressure to 200 bar, and at temperatures in the range from 20° C. to 200° C. Pressure ranges between atmospheric pressure and 120 bar, and temperatures in the range from 50° to 140° C., are preferred.

The alkoxymethylenenitrilomalonates of the formula (XIII) and the halogenoacrylonitrile derivatives of the formula (XV) are generally known compounds of organic chemistry.

Formula (III) provides a general definition of the acylating agent furthermore required as starting substances for carrying out process (a−α) according to the invention. In this formula (III), R⁴ and X preferably stand for those radicals which have already been mentioned in connection with the description of the substances of the formula (I) according to the invention as being preferred for these substituents.

E¹ preferably stands for halogen, in particular for chlorine or bromine or for a radical

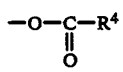

wherein $R^4$ has the abovementioned meaning.

The acylating agents of the formula (III) are generally known compounds of organic chemistry.

Formula (IV) provides a general definition of the sulphenylating, sulphinylating or sulphonylating agents furthermore required as starting substances for carrying out process (a—β) according to the invention. In this formula (IV), $R^5$ and n preferably stand for those radicals and indices which have already been mentioned in connection with the description of the substances of the formula (I) according to the invention as being preferred for this substituent and this index.

$E^2$ preferably stands for halogen, in particular for fluorine, chlorine or bromine.

The sulphenylating, sulphinylating and sulphonylating agents are also generally known compounds of organic chemistry.

Formula (V) provides a general definition of the alkylating agents furthermore required as starting substances for carrying out process (a—γ) according to the invention. In this formula (V), $R^{3-2}$ preferably stands for straight-chain or branched alkyl having 1 to 6, in paritcular having 1 to 4 carbon atoms.

$E^3$ preferably stands for halogen, in particular for bromine or iodine, for alkoxysiulphonyloxy or for optionally substituted arylsulphonyloxy, such as, for example methoxysulphonyloxy, ethoxysulphonyloxy or p-toluenesulphonyloxy.

The alkylating agents of the formula (V) are also generally known compounds of organic chemistry.

Formula (VI) provides a general definition of the iso(thio)cyanates furthermore required as starting substances for carrying out process (b) according to the invention.

In this formula (VI), X preferably stands for those radicals which have already been mentioned in connection with the description of the substances of the formula (I) according to the invention as being preferred for this substituent.

$R^6$ preferably stands for straight-chain or branched alkyl having 1 to 4 carbon atoms or for phenyl which is optionally monosubstituted, disubstituted or trisubstituted by identical or different substituents, suitable substituents being: halogen, in each case being straightchain or branched alkyl or alkoxy having in each case 1 to 4 carbon atoms, or halogenoalkyl having 1 to 4 carbon atoms and 1 to 9 identical or different halogen atoms. $R^6$ in particular stands for methyl, ethyl or phenyl which is optionally monosubstituted, disubstituted or trisubstituted by identical or different substituents from the series comprising fluorine, chlorine, methyl methoxy or trifluoromethyl.

The iso(thio)cyanates of the formula (VI) are also generally known compounds of organic chemistry.

Formula (Iz) provides a general definition of the 1-arylpyrazoles required as starting substances for carrying out process (c) according to the invention. In this formula (Iz), $R^2$, $R^3$ and Ar preferably stand for those radicals which have already been mentioned in connection with the description of the substances of the formula (I) according to the invention as being preferred for these substituents.

The 1-arylpyrazoles of the formula (Iz) are compounds according to the invention and can be obtained with the aid of processes (a), (b), (d), (f) and (g) according to the invention.

Formula (Iy) provides a general definition of the 1-arylpyrazoles required as starting substances for carrying out process (d) according to the invention. In this formula (Iy), $R^1$, $R^4$ and Ar preferably stand for those radicals which have already been mentioned in connection with the description of the substances of the formula (I) according to the invention as being preferred for these substituents.

$R^{3-2}$ preferably stands for straight-chain or branched alkyl having 1 to 6, in particular having 1 to 4 carbon atoms.

The 1-arylpyrazoles of the formula (Iy) are also compounds according to the invention and can be obtained with the aid of processes (a—γ) or (c) according to the invention.

Formula (Ix) provides a general definition of the 1-arylpyrazoles required as starting substances for carrying out process (e) according to the invention. In this formula (Ix), $R^5$ and Ar preferably stand for those radicals which have already been mentioned in connection with the description of the substances of the formula (I) according to the invention as being preferred for these substitutents.

The 1-arylpyrazoles of the formula (Ix) are also compounds according to the invention and can be obtained with the aid of process (a—β) according to the invention.

Formula (Iw) provides a general definition of the 1-arylpyrazoles required as starting substances for carrying out process (f) according to the invention. In this formula (Iw), $R^1$ and Ar preferably stand for those radicals which have already been mentioned in connection with the description of the substances of the formula (I) according to the invention as being preferred for these substituents.

$R^7$ preferably stands for phenyl which is optionally monosubstituted, disubstituted or trisubstituted by halogen and/or lower alkyl, in particular for unsubstituted phenyl, $R^{2-1}$ preferably stands for hydrogen or for a radical

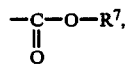

$R^7$ having the abovementioned meaning.

The 1-arylpyrazoles of the formula (Iw) are also compounds according to the invention and can be obtained with the aid of processes (a—α) or (c) according to the invention.

Formula (VII) provides a general definition of the alcohols, amines or thiols furthermore required as starting substances for carrying out process (f) according to the invention. In this formula (VII), $R^{4-1}$ preferably stands for alkoxy, alkylthio, alkylamino or dialkylamino, in each case straight-chain or branched and in each case having 1 to 4 carbon atoms in the individual alkyl moieties, or for phenoxy, phenylthio or phenylamino, in each case optionally monosubstituted or polysubstituted by identical or different substitutents suitable phenyl substituents being in each case: halogen, alkyl or alkoxy, both straight-chain or branced and both having 1 to 4 carbon atoms, or halogenoalkyl having 1 to 4 carbon atoms and 1 to 9 identical or different halogen atoms, in particular methyl, methoxy, chlorine or trifluoromethyl; $R^{4-1}$ particularly stands for methoxy, ethoxy, methylthio, phenylthio or dimethylamino.

The alcohols, amines or thiols of the formula (VII) are generally known compounds of organic chemistry.

Formula (VIII) provides a general definition of the 5-halogeno-1-aryl-pyrazoles required as starting substances for carrying out process (g) according to the invention. In this formula (VIII), $R^1$ and Ar preferably stand for those radicals which have already been mentioned in connection with the description of the substances of the formula (I) according to the invention as being preferred for these substituents. $Hal^1$ preferably stands for chlorine or bromine.

The 5-halogeno-1-aryl-pyrazoles of the formula (VIII) were hitherto unknown. They can, however, be obtained in analogy to known processes (cf. European Patent Specification No. 191,282), for example, by reacting alkoxymethylenemalonates of the formula (XVI)

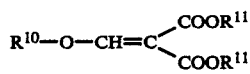
(XVI)

in which
$R^{10}$ and $R^{11}$ independently of one another each stand for alkyl, in particular for methyl or ethyl,
with arylhydrazines of the formula (XII)

 (XII)

in which
Ar has the abovementioned meaning,
initially in a first step, if appropriate in the presence of a diluent such as, for example, methanol or ethanol, at temperatures between $+10°$ C. and $+80°$ C., and by hydrolysing and decarboxylating the pyrazole carboxylates of the formula (XVII)

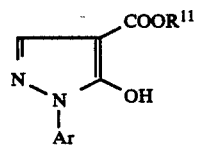
(XVII)

in which
$R^{11}$ and Ar have the abovementioned meanings, obtainable in this way, in a 2nd step, if appropriate in the presence of a diluent such as, for example, methanol, and if appropriate in the presence of a base such as, for example, sodium hydroxide, at temperatures between $+30°$ C. and $+70°$ C., to give pyrazolinones of the formula (XVIII)

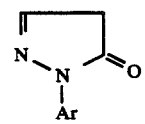
(XVIII)

in which
Ar has the abovementioned meaning,
and by reacting these compounds in a 3rd step with halogenating agents such as, for example, phosphorus oxychloride or phosphorus oxybromide, by customary known processes (cf., for example, Ber. dtsch. Chem. Ges., 28, 35 (1985) or Liebigs Ann. Chem., 373, 129 (1910)) and, if appropriate, nitrating the 5-halogeno-pyrazoles of the formula (VIIIa)

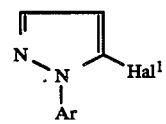
(VIIIa)

in which
$Hal^1$ and Ar have the abovementioned meanings, obtainable in this way, in a 4th step in analogy to the method of carrying out process (c) according to the invention using nitric acid, if appropriate in the presence of a diluent such as, for example, glacial acetic acid, and if appropriate in the presence of a catalyst or reaction auxiliary such as, for example, acetic anhydride, at temperatures between $-20°$ C. and $+50°$ C.

If appropriate, the intermediates of the formula (XIX)

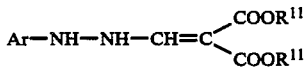
(XIX)

in which
Ar and $R^{11}$ have the abovementioned meanings, occurring during the reaction of alkoxymethylenemalonates of the formula (XVI) with aryl hydrazines of the formula (XII), may also be ioslated and, in a separate reaction step, cyclized.

Cyclization to give the pyrazole carboxylates of the formula (XVII) and their subsequent decarboxylation can be carried out, it appropriate, in one reaction step as a "one-pot process" (cf. for example, Liebigs Ann. Chem., 373, 142 (1910)).

The alkoxymethylenemalonates of the formula (XVI) are generally known compounds of organic chemistry.

Formula (IX) provides a general definition of the amines furthermore required as starting substances for carrying out process (g) according to the invention. In this formula (IX), $R^{3-2}$ preferably stands for straight-chain or branched alkyl having 1 to 6 carbon atoms, in particular for methyl, ethyl, n- or i-propyl, or n-, i-, s- or t-butyl.

The amines of the formula (IX) are generally known compounds of organic chemistry.

Formula (Iv) provides a general definition of the 1-arylpyrazoles required as starting substances for carrying out process (h) according to the invention. In this formula (Iv), $R^1$ and Ar preferably stand for those radicals which have already been mentioned in connection with the description of the substances of the formula (I) according to the invention as being preferred for those substituents.

$R^{2-2}$ preferably stands for a radical $-SO_2-R^5$, wherein $R^5$ preferably stands for those radicals which have already been mentioned in connection with the description of the substances of the formula (I) according to the invention as being preferred for this substituent.

The 1-arylpyrazoles of the formula (Iv) are compounds according to the invention and can be obtained with the aid of processes (a—α), (a—β), (c), (e) or (f) according to the invention.

Formula (X) provides a general definition of the salts furthermore required as starting substances for carrying out process (h) according to the invention. Akali metal, alkaline earth metal, ammonium or transition metal hydroxides, oxides, carbonates, bicarbonates, or readily soluble chlorides, sulphates, phosphates or nitrates, such as, for example, the hydroxides, carbonates or bicarbonates of sodium, potassium or calcium, calcium chloride, barium chloride, copper sulphate, nickel chloride or cobalt nitrate, or alkylamines, such as triethylamine, isopropylamine, diisopropylamine or butylamine, are preferably used.

The salts of the formula (X) are generally known compounds of organic chemistry.

Suitable diluents for carrying out process (a) according to the invention are inert organic solvents. Aliphatic, alicyclic or aromatic, optionally halogenated hydrocarbons such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl ether or ethylene glycol dimethyl ether, ketones, such as acetone, butanone, methyl isopropyl ketone or methyl isobutyl ketone, esters, such as ethyl acetate, acids, such as acetic acid, nitriles, such as acetonitrile or propionitrile, amides, such as dimethylformamide, dimethylacetamide, n-methyl-pyrrolidone or hexamethylphosphoric triamide are preferably used. If, as reaction partners in the variants (a—α), (a=β) or (a=γ), compounds of the formulae (III), (IV) or (V) are used in their liquid form, it is also possible for these to be employed simultaneously as a diluent in suitable excess.

Suitable reaction auxiliaries for carrying out process (a) according to the invention are all customarily useable inorganic and organic bases. Alkali metal hydrides, hydroxides, amides, carbonates or bicarbonates, such as, for example, sodium hydride, sodium amide, sodium hydroxide, sodium carbonate or sodium bicarbonate, and also tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU) are preferably used.

When carrying out process (a) according to the invention, the reaction temperatures may be varied within a relatively wide range. In general, the process is carried out between −20° C. and +150° C., preferably between 0° C. and +100° C.

For carrying out process (a) according to the invention, in general, 1.0 to 20.0 moles each, preferably 1.0 to 15.0 moles each, of acylating agent of the formula (III) or sulphenylating or sulphinylating or sulphonylating agent of the formula (IV) or alkylating agent of the formula (V) and if appropriate 1.0 to 3.0 moles, preferably 1.0 to 2.0 moles, of reaction auxiliary are employed per mole of 1-arylpyrazole of the formula (II) in the variants (a—α), (a—β) or (a—γ). The reaction is carried out, and the reaction products of the formula (Ia) are worked up and isolated by customary methods.

Suitable diluents for carrying out process (b) according to the invention are inert organic solvents. The diluents mentioned in process (a) are preferably used. If iso(thio)cyanates of the formula (VI) are used in their liquid form, it is also possible for these to be employed simultaneously as diluents in suitable excess.

Suitable reaction auxiliaries for carrying out process (b) according to the invention are tertiary amines, such as, for example, triethylamine, N,N-dimethylaniline, pyridine, 4-(N,N-dimethylamino)-pyridine, diazabicyclooctane (DABCO), diazabcyclonones (DBN) or diazabicycloundecene (DBU).

When carrying out process (b) according to the invention, the reaction temperatures may be varied within a relatively wide range. In general, the process is carried out between −20° C. and +150° C., preferably between 0° C. and +100° C.

For carrying out process (b) according to the invention, in general, 1.0 to 20.0 moles, preferably 1.0 to 15.0 moles of iso(thio)cyanate of the formula (VI) and if appropriate 1.0 to 3.0 moles, preferably 1.0 to 2.0 moles, of reaction auxiliary are employed per mole of 1-arylpyrazole of the formula (II). The reaction is carried out, and the reaction products of the formula (Ib) are worked up and isolated by customary methods.

Suitable diluents for carrying out process (c) according to the invention are all solvents customarily useable for nitrations of this type. The acids or mixtures suitable as reactants such as, for example, sulphuric acid, nitric acid or nitrating acid, are preferably simultaneously used as diluents. If appropriate, inert organic solvents such as, for example, glacial acetic acid, or chlorinated hydrocarbons such as methylene chloride, chloroform or carbon tetrachloride, are also suitable as diluents.

Suitable reaction auxiliaries for carrying out process (c) according to the invention are also the customary catalysts for nitrations of this type; acid catalysts such as, for example, sulphuric acid or acetic anhydride, are preferably used.

When carrying out process (c) according to the invention, the reaction temperatures may be varied within a relatively wide range. In general, the process is carried out between −50° C. and +200° C., preferably between −20° C. and +150° C.

For carrying out process (c) according to the invention, in general, 1.0 to 10.0 moles, preferably 1.0 to 5.0 moles of nitric acid and if appropriate 0.1 to 10 moles of reaction auxiliary are employed per mole of 1-arylpyrazole of the formula (Iz). The reaction is carried out, and the reaction products of the formula (Ic) are worked up and isolated in a generally customary manner.

Suitable diluents for carrying out process (d) according to the invention are inorganic or organic polar solvents. Alcohols such as, for example, methanol, ethanol or propanol, or aqueous mixtures thereof, are preferably used.

Suitable reaction auxiliaries for carrying out process (d) according to the invention are acids, in particular hydrochloric acid or sulphuric acid.

When carrying out process (d) according to the invention, the reaction temperatures may be varied within a relatively wide range. In general, the process is carried out between +20° C. and +150° C., preferably between +50° C. and +120° C.

For carrying out process (d) according to the invention, in general, 1.0 to 20.0 moles, preferably 1.0 to 10.0 moles of catalytic acid are employed per mole of 1-arylpyrazole of the formula (Iy), and the mixture is heated at the required reaction temperature for several hours. The reaction products of the formula (Id) are worked up, isolated and purified by customary methods.

Suitable diluents for carrying out process (e) according to the invention are polar organic solvents or aqueous mixtures thereof. Alcohols such as methanol, ethanol or propanol, or aqueous mixtures thereof, are preferably used.

Suitable reaction auxiliaries for carrying out process (e) according to the invention are all customary inorganic or organic bases. Amines, or ammonia solutions, or alkali metal carbonates, or alkali metal bicarbonates, such as sodium or potassium carbonate or sodium bicarbonate, are preferably used.

When carrying out process (e) according to the invention, the reaction temperatures may be varied within a relatively wide range. In general, the process is carried out between 0° C. and 80° C., preferably between 20° C. and 40° C.

For carrying out process (e) according to the invention, in general, 1.0 to 30.0 moles, preferably 1.0 to 15.0 moles, of base are employed per mole of 1-aryl-pyrazole of the formula (Ix). Stirring of the reaction mixture is carried out in a suitable diluent until it is no longer possible to detect any starting material by chromatographic monitoring (30 minutes to 20 hours). The reaction products of the formula (Ie) are worked up and isolated by customary methods.

Suitable diluents for carrying out processes (f) according to the invention are inert organic solvents. Aliphatic or aromatic hydrocarbons which are optionally halogenated, such as benzine, benzene, toluene, xylene, pentane, hexane, heptane, cyclohexane, petroleum ether, ligroin, methylene chloride, ethylene chloride, chloroform, carbon tetrachloride, chlorobenzene or dichlorobenzene, ethers, such as diethyl ether or diisopropyl ether, ethylene glycol dimethyl ether, tetrahydrofuran or dioxane, ketones, such as acetone or butanone, methyl isopropyl ketone or methyl isobutyl ketone, esters, such as ethyl acetate, nitriles, such as acetonitrile or propionitrile, amides, such as dimethylformamide, dimethylacetamide, N-methylpyrrolidone or hexamethylphosphoric triamide, or alcohols such as methanol, ethanol or isopropanol, are preferably used. It is, however, also possible for the alcohols, amines or thiols of the formula (VII) used as reaction components to be employed simultaneously as diluents in suitable excess.

If appropriate, process (f) according to the invention can be carried out in the presence of a basic reaction auxiliary. Suitable auxiliaries are all customary inorganic or organic bases. Alkali metal hydroxides such as sodium hydroxide or potassium hydroxide, alkali metal carbonates such as sodium carbonate, potassium carbonate or sodium bicarbonate, and also tertiary amines such as triethylamine, N,N-dimethylaniline, pyridine, N,N-dimethylaminopyridine, diazabicyclooctane (DABCO), diazabicyclononene (DBN) or diazabicycloundecene (DBU), are preferably used.

When carrying out process (f) according to the invention, the reaction temperatures may be varied within a relatively wide range. In general, the process is carried out between 0° C. and +200° C., perferably between +20° C. and +150° C.

For carrying out process (f) according to the invention, in general, 1 to 20 moles, preferably 1 to 10 moles, of alcohol, amine or thiol of the formula (VII), and if appropriate 0.1 to 2 moles, preferably 0.1 to 1 mole, of reaction auxiliary are employed per mole of 1-aryl-pyrazole of the formula (Iw), and the mixture is heated at the required temperature for several hours. The reaction products of the formula (If) are worked up and isolated by customary methods.

Suitable diluents for carrying out process (g) according to the invention are inert organic solvents. These include in particular aliphatic or aromatic hydrocarbons which are optionally halogenated, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethylsulphoxide.

If appropriate, process (g) according to the invention can be carried out in the presence of a suitable reaction auxiliary.

Suitable auxiliaries are all customary inorganic or organic bases. These include, for example, alkali metal hydroxides, such as sodium hydroxide or potassium hydroxide, alkali metal carbonates, such as sodium carbonate, potassium carbonate or sodium bicarbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU). It is, however, also possible for the amine of the formula (IX) employed as a reaction partner to be used simultaneously as a reaction auxiliary in a suitable excess.

When carrying out process (g) according to the invention, the reaction temperatures may be varied within a relatively wide range. In general, the process is carried out at temperatures between −20° C. and +200° C., preferably at temperatures between 0° C. and +150° C.

For carrying out process (g) according to the invention, in general, 1.0 to 10.0 moles, preferably 1.0 to 5.0 moles, of amine of the formula (IX) are employed per mole of 5-halogeno-1-arylpyrazole of the formula (VIII). The reaction is carried out and the reaction products of the formula (Ig) are worked up and isolated by generally customary methods.

Suitable diluents for carrying out process (h) according to the invention are polar organic solvents, water or aqueous mixtures. Alcohols such as, for example, methanol, ethanol or propanol, aqueous mixtures thereof or pure water, are preferably used.

When carrying out process (h) according to the invention, the reaction temperatures may be varied within a relatively wide range. In general, the process is carried out between 0° C. and +80° C., preferably between +20° C. and +40° C.

For carrying out process (h) according to the invention, in general, 1.0 to 10 moles, preferably 1.0 to 5.0 moles, of salt of the formula (X) or of amine are employed per mole of 1-aryl-pyrazole of the formula (Iv). For the preparation of the sodium, potassium or ammonium salts, a compound of the formula (Iv) is reacted with sodium hydroxide, potassium hydroxide or ammonium hydroxide or an amine, either in an aqueous solution or in an organic solvent, such as acetone, methanol, ethanol or dimethylformamide, and the salts are isolated by filtration or by evaporation of the solution, and, if appropriate, are purified by recrystallization. The calcium, barium, magnesium, manganese, copper, nickel, tin, iron or cobalt salts are prepared from the sodium salts by treating with a suitable inorganic metal salt, for example calcium chloride, barium chloride, copper sulphate, nickel chloride or cobalt nitrate. The calcium salts can also be prepared by treating of a compound of the formula (Iv) with calcium hydroxide.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotina, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used with particularly good success for selectively combating monocotyledon and dicotyledon weeds, in monocotyledon and dicotyledon cultures, such as, for example, wheat, barley, rye, rice, corn, cotton or soya beans.

The precursors of the formula (VIII), also have a good herbicidal activity.

At appropriate application rates, the active compounds according to the invention also exhibit a broad fungicidal activity and can be employed, for example, for combating scab fungi (Venturia species) of for combating downy mildew fungi in fruit and vegetable growing, and for combating rice disease, such as, for example, against the pathogen of rice spot (Pyricularia oryzae).

Moreover, the active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polar substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example, ammonium salts and ground natural minerals, such as kaolins, clays, talc, chalk, quartz, attapulgite, montmorillonite or diatomaceous earth, and ground synthetic minerals, such as highly-disperse silicic acid, alumina and silicates, as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example, alkylaryl polyglycol ethers, alkylsulphonates, alkyl sulphates, arylsulphonates as well as albumen hydrolyzation products; as dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N′-dimethylurea for combating weeds in cereals; 4-amino-3-methyl-6-phenyl-1,2,4-triazin-5(4H)-one for combating weeds in sugar beet, and 4-amino-6-(1,1-dimethylethyl)-3-methylthio-1,2,4-triazin-5(4H)-one for combating weeds in soya beans.

Mixtures with 5-(2-chloro-4-trifluoromethylphenoxy-2-nitro-benzoic acid; N-(methoxymethyl)-2,6-diethyl chloroacetanilide; methyl-6,6-dimethyl-2,4-dioxo-3-[1-(2-propenyloxyamino)-butylidene]-cyclohexanecarboxylic acid; 2-chloro-4-ethylamino-6-isopropylamino-1,3,5-triazine; 3-isopropyl-2,1,3-benzothiadiazin-4-one-2,2-dioxide; methyl-5-(2,4-dichlorophenoxy)-2-nitrobenzoate; 3,5-dibromo-4-hydroxy-benzonitrile; 2-chloro-N-}[(4-methoxy-6-methyl-1,3,5-triazin-2-yl)-amino]-carbonyl}-benzenesulphonamide; N,N-dimethyl-N′-(3-chloro-4-methylphenyl)-urea; exo-1-methyl-4-(1-methylethyl)-2-(2-methylphenyl-methoxy)-7-oxabicyclo-(2,2,1)-heptane; ethyl-2-{[(4-chloro-6-methoxy-2-pyrimidinyl)-aminocarbonyl]-aminosulphonyl}-benzoate; 2-chloro-4-ethylamino-6-(3-cyanopropylamino)-1,3,5-triazine; S-ethyl N,N-di-n-propyl-thiocarbamate; 4-amino-6-t-butyl-3-ethylthio-1,2,4-triazin-5(4H)-one; 2-{4-[(6-chloro-2-benzoxazolyl)-oxy]-phenoxy}-propanoic acid and methyl ester or ethyl ester thereof; trimethylsilylmethyl 2-[4-(3,5-dichloropyrid-2-yloxy)-phenoxy]-propionate; 5-(2-chloro-4-trifluoromethyl-phenoxy)-N-methylsulphonyl-2-nitrobenzamide; N-phosphonomethyl-glycine; 2-{4-[(3-chloro-5-(trifluoromethyl)-2-pyridinyl)-oxy]-phenoxy}-propanoic acid or ethyl 2-{4-[(3-chloro-5-(trifluoromethyl)-2-pyridinyl)-oxy]-phenoxy}-propanoate; methyl 2-[4-(2,4-dichlorophenoxy)-phenoxy]-propionate; methyl 2-[4,5-dihydro-4-methyl-4-(1-methylethyl)-5-oxo-1H-imidazol-2yl]-4(5)-methylbenzoate; 3,5-diiodo-4-hydroxybenzonitrile; N,N-dimethyl-N′-(4-isopropylphenyl)-urea; (2-methyl-4-chlorophenoxy)-acetic acid; (4-chloro-2-methylphenoxy)-propionic acid; 2,4-dichlorophenoxyacetic acid; 2,4-dichlorophenoxypropionic acid; N-methyl-2-(1,3-benzothiazol-2-yloxy)-acetanilide; 2-chloro-N-(2,6-dimethylphenyl)-N-[(1H)-pyrazol-1-yl-methyl]-acetamide; 2-ethyl-6-methyl-N-(1-methyl-2-methoxyethyl)-chloroacetanilide; 2-{[[((4-methoxy-6-methyl-1,3,5-triazin-2-yl)-amino)-carbonyl]-amino]-sulphonyl}-benzoic acid or the methyl ester thereof; N-(1-ethylpropyl)-3,4-dimethyl-2,6-dinitroaniline; 3-(ethoxycarbonylaminophenyl)-N-(3′-methyl-phenyl)-carbamate; α-chloro-2′,6′-diethyl-N-(2-propoxyethyl)-acetanilide; 0-(6-chloro-3-phenyl-pyridazin-4-yl)-S-octyl thiocarbonate; 2-[1-(ethoxamino)-butylidene]-5-(2-ethylthiopropyl)-1,3-cyclohexadione; 2-chloro-4,6-bis-(ethylamino)-1,3,5-triazine; methyl 2-{[(4,6-dimethyl-2-pyrimidinyl)-aminocarbonyl]-aminosulphonyl}-benzoate; 4-ethylamino-2-t-butylamino-6-methylthio-s-triazine; S-(2,3,3-trichloroally)-N,N-diisoproyl-thiolcarbamate, or 2,6-dinitro-4-trifluoromethyl-N,N-dipropylaniline are also advantageous. Some mixtures surprisingly also exhibit a synergistic effect.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example, by watering, spraying, atomizing or scattering.

The active compounds according to the invention can be applied either before or after emergence of the plants.

They can also be incorporated into the soil before sowing.

When using the compounds according to the invention as herbicides the amount of active compound used, can vary within a substantial range. It depends essentially on the nature of the desired effect. In general, the amounts used are between 0.01 and 10 kg of active compound per hectare of soil surface, preferably between 0.05 and 5 kg per ha.

When used as plant-growth regulators, the compounds according to the invention can likewise be used in amounts which vary within a substantial range.

In general, 0.01 to 50 kg, preferably 0.05 to 10 kg, of active compound are employed per hectare of soil surface.

As regards the time of application, the rule is that the growth regulators are applied within a preferred period of time, the exact definition of which depends on the climatic and vegetative circumstances.

Preparation examples:

EXAMPLE 1:

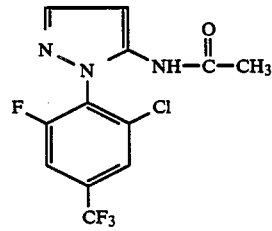

(Process a—α)

3.7 ml (0.038 mol) of acetic anhydride are added to 100 g (0.036 mol) of 5-amino-1-(2-chloro-6-fluoro-4-trifluoromethylphenyl)-pyrazole in 60 ml of glacial acetic acid, and the mixture is stirred at room temperature for 9 hours. For working-up, the reaction mixture is added dropwise to 300 ml of ice-water, and the precipitate formed is filtered off, washed with water and dried in vacuo at 50° C. 8.9 g (77% of theory) of 5-acetamido-1-

(2-chloro-6-fluoro-4-trifluoromethylphenyl)-pyrazole of melting point 144°-146° C. are obtained.

EXAMPLE 2:

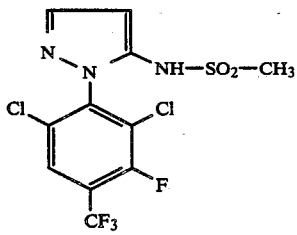

(Process a—β/e)

3.2 ml (0.041 mol) of 99 percent strength methanesulphonyl chloride are added to a solution of 6.3 g (0.02 mol) of 5-amino-1-(2,6-dichloro-3-fluoro-4-trifluoromethyl-phenyl)-pyrazole in 30 ml of anhydrous pyridine at 0° C. The mixture is stirred at room temperature for 16 hours and then poured into approximately 400 ml of ice-water. 200 ml of dichloromethane are added, and the organic phase is separated off, washed with dilute hydrochloric acid, and the solvent is removed in vacuo. The residue is dissolved in 75 ml of ethanol, 15 ml of concentrated ammonia solution are added and the mixture is stirred for 24 hours at 0° C.-5° C. The ethanol is removed in vacuo, the residue is extracted using dichloromethane, and the organic phase is washed successively with dilute hydrochloric acid, saturated sodium bicarbonate solution and saturated sodium chloride solution. After the solvent has been removed in vacuo, 5.3 g (68% of theory) of 5-methanesulphonamido-1-(2,6-dichloro-3-fluoro-4-trifluoromethylphenyl)-pyrazole of melting point 141°-143° C. are obtained.

EXAMPLE 3:

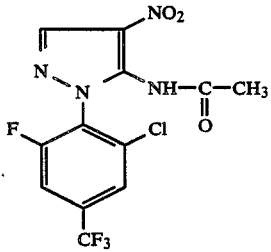

(Process c)

2 ml (0.021 mol) of acetic anhydride and 0.9 ml (0.02 mol) of 98% strength nitric acid are successively added to 6 g (0.019 mol) of 5-acetamido-1-(2-chloro-6-fluoro-4-trifluoromethylphenyl)-pyrazole in 15 ml of glacial acetic acid at room temperature, and the mixture is stirred at room temperature for 15 hours. For working-up, the reaction mixture is added dropwise to 200 ml of ice-water, and the precipitate formed is filtered off, washed with water and dried in vacuo at 50° C. 5.8 g (85% of theory) of 5-acetamido-4-nitro-1-(2-chloro-6-fluoro-4-trifluoromethylphenyl)-pyrazole of melting point 129°-130° C. are obtained.

EXAMPLE 4:

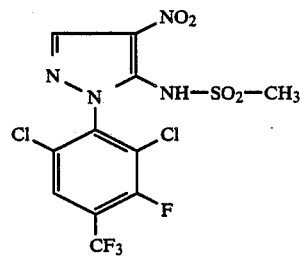

(Process c)

1.07 ml (0.011 mol) of acetic anhydride and 0.45 ml (0.0106 mol) of 98 percent strength nitric acid are added successively to a solution of 3.8 g (0.01 mol) of 5-methanesulphonamido-1-(2,6-dichloro-3-fluoro-4-trifluoromethylphenyl)-pyrazole in 20 ml of glacial acetic acid at approximately 15° C. The mixture is stirred at room temperature for approximately 16 hours, and the reaction solution is then poured into 100 ml of water. The precipiate thus formed is filtered off with suction, washed until neutral and dried in vacuo. 3.5 g (80% of theory) of 5-methanesulphonamido-4-nitro-1-(2,6-dichloro-3-fluoro-4-trifluoromethylphenyl)-pyrazole of melting point 107°-115° C. are obtained.

In a corresponding manner and according to the general instructions for the preparation, the following 1-aryl-pyrazoles of the general formula (I)

$$\text{(I)}$$

are obtained:

TABLE 1

| Ex. No. | $R^1$ | $R^2$ | $R^3$ | Ar | Physical properties |
|---|---|---|---|---|---|
| 5 | H | H | —CO—$C_2H_5$ | 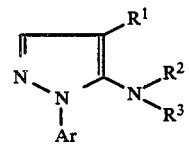 | m.p.: 75–85° C. |

TABLE 1-continued

| Ex. No. | R¹ | R² | R³ | Ar | Physical properties |
|---|---|---|---|---|---|
| 6 | NO₂ | H | —CO—C₂H₅ | 2,5-dichloro-3-fluoro-4-(trifluoromethyl)phenyl | m.p.: 77–80° C. |
| 7 | H | H | —CO—CH₃ | 2,5-difluoro-4-(trifluoromethyl)phenyl | m.p.: 109–111° C. |
| 8 | NO₂ | H | —CO—CH₃ | 2,5-difluoro-4-(trifluoromethyl)phenyl | m.p.: 158–160° C. |
| 9 | H | H | —CO—CH₃ | 2-fluoro-5-chloro-4-(trifluoromethyl)phenyl | m.p.: 87–90° C. |
| 10 | H | H | —CO—CH₃ | 2-chloro-3-fluoro-4-(trifluoromethyl)phenyl | m.p.: 126–128° C. |
| 11 | NO₂ | H | —CO—CH₃ | 2-chloro-3-fluoro-4-(trifluoromethyl)phenyl | m.p.: 73–77° C. |
| 12 | H | H | —CO—CH₃ | 2,5-dichloro-3-fluoro-4-(trifluoromethyl)phenyl | m.p.: 146–149° C. |
| 13 | NO₂ | H | —CO—CH₃ | 2,5-dichloro-3-fluoro-4-(trifluoromethyl)phenyl | m.p.: 67–70° C. |
| 14 | H | H | —CO—H | 2-chloro-5-fluoro-4-(trifluoromethyl)phenyl | m.p.: 93–109° C. |

TABLE 1-continued
| Ex. No. | R¹ | R² | R³ | Ar | Physical properties |
|---|---|---|---|---|---|
| 15 | H | H | —CO—(CH₂)₂—CH₃ | 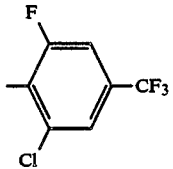 | m.p.: 84–86° C. |
| 16 | H | H | —SO₂—CH₃ | 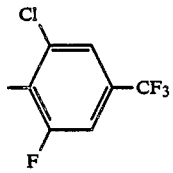 | ¹H-NMR* 2.95(s); 7.05(s); 7.45(dd) |
| 17 | H | H | —CO—CH(Cl)—CH₃ | 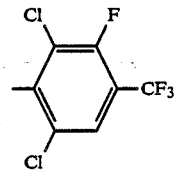 | m.p.: 74–79° C. |
| 18 | H | H | —CO—(CH₂)₂—CH₃ | 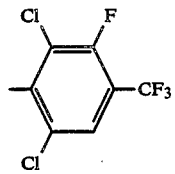 | m.p.: 117–120° C. |
| 19 | H | H | —CO—CH₂—OCH₃ | 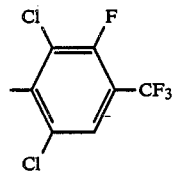 | m.p.: 91–93° C. |
| 20 | H | H | —CO—H | 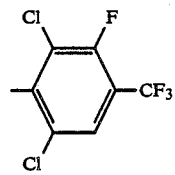 | m.p.: 89–107° C. |
| 21 | H | H | —CO—OCH₃ | 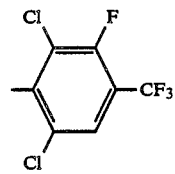 | m.p.: 69–76° C. |
| 22 | H | H | —CO—CH₂—OCH₃ | 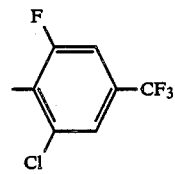 | m.p.: 96° C. |
| 23 | H | H | —CO—OCH₃ | 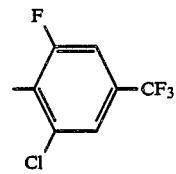 | m.p.: 103–105° C. |

TABLE 1-continued

| Ex. No. | R¹ | R² | R³ | Ar | Physical properties |
|---|---|---|---|---|---|
| 24 | $NO_2$ | H | $-CO-\underset{\underset{CH_3}{\|}}{\overset{\overset{Cl}{\|}}{CH}}$ | 2,6-dichloro-3-fluoro-4-(trifluoromethyl)phenyl (Cl, F, CF₃, Cl) | m.p.: 79–81° C. |
| 25 | $NO_2$ | H | $-CO-(CH_2)_2-CH_3$ | 2,6-dichloro-3-fluoro-4-(trifluoromethyl)phenyl | m.p.: 66–68° C. |
| 26 | $NO_2$ | H | $-CO-CH_2-OCH_3$ | 2,6-dichloro-3-fluoro-4-(trifluoromethyl)phenyl | m.p.: 85–87° C. |
| 27 | $NO_2$ | H | $-SO_2-CH_3$ | 2-chloro-5-fluoro-4-(trifluoromethyl)phenyl | m.p.: 95° C. |
| 28 | $NO_2$ | H | $-CO-H$ | 2,6-dichloro-3-fluoro-4-(trifluoromethyl)phenyl | m.p.: 159–171° C. |
| 29 | $NO_2$ | H | $-CO-OCH_3$ | 2,6-dichloro-3-fluoro-4-(trifluoromethyl)phenyl | m.p.: 91–104° C. |
| 30 | $NO_2$ | H | $-CO-CH_2-OCH_3$ | 3-fluoro-5-chloro-4-(trifluoromethyl)phenyl | m.p.: 144–146° C. |
| 31 | $NO_2$ | H | $-CO-OCH_3$ | 3-fluoro-5-chloro-4-(trifluoromethyl)phenyl | ¹H-NMR* 8.32 |

TABLE 1-continued

| Ex. No. | R¹ | R² | R³ | Ar | Physical properties |
|---|---|---|---|---|---|
| 32 | NO₂ | H | —CO—CH₃ | (phenyl: F, CF₃, Cl) | m.p.: 154–157° C. |
| 33 | NO₂ | H | —CO—H | (phenyl: F, CF₃, Cl) | m.p.: 60–65° C. |
| 34 | NO₂ | H | —CO—(CH₂)₂—CH₃ | (phenyl: F, CF₃, Cl) | m.p.: 68–73° C. |
| 35 | H | H | —CO—CH₃ | (phenyl: Cl, F, CF₃, F) | m.p.: 49–55° C. |
| 36 | NO₂ | H | —CO—CH₃ | (phenyl: Cl, F, CF₃, F) | m.p.: 85–95° C. |
| 37 | H | H | —CO—CH(Cl)—CH₃ | (phenyl: Cl, F, CF₃) | m.p.: 97–100° C. |
| 38 | H | H | —CO—CH(Cl)—CH₃ | (phenyl: Cl, CF₃, F) | m.p.: 107–108° C. |
| 39 | NO₂ | H | —CO—CH(Cl)—CH₃ | (phenyl: Cl, F, CF₃) | m.p.: 83–86° C. |
| 40 | NO₂ | H | —CO—CH(Cl)—CH₃ | (phenyl: Cl, CF₃, F) | ¹H-NMR* 8.38 |

TABLE 1-continued
| Ex. No. | $R^1$ | $R^2$ | $R^3$ | Ar | Physical properties |
|---|---|---|---|---|---|
| 41 | H | H | —CO—CH$_2$—OCH$_3$ | 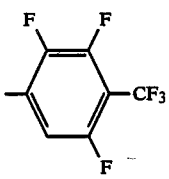 | m.p.: 58–61° C. |
| 42 | NO$_2$ | H | —CO—CH$_2$—OCH$_3$ | 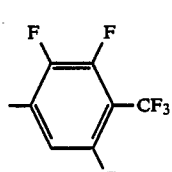 | m.p.: 97–98° C. |
| 43 | NO$_2$ | H | —CO—C$_2$H$_5$ | 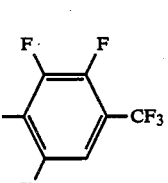 | m.p.: 126° C. |
| 44 | NO$_2$ | H | —CO—C$_2$H$_5$ | 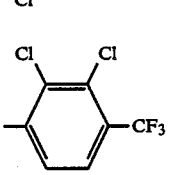 | m.p.: 91° C. |
| 45 | NO$_2$ | H | —CO—CH$_2$—OCH$_3$ | 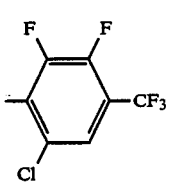 | m.p.: 99° C. |
| 46 | NO$_2$ | H | —CO—CH$_2$—OCH$_3$ | 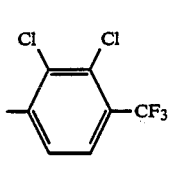 | $^1$H-NMR* 3.5(s) |
| 47 | NO$_2$ | H | —CO—CH$_3$ | 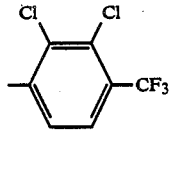 | m.p. 109–117° C. |
| 48 | H | H | —CO—CH(Cl)—CH$_3$ | 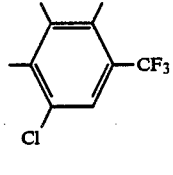 | $^1$H-NMR* 4.45(q) |
| 49 | H | H | —CO—CH(Cl)—CH$_3$ | 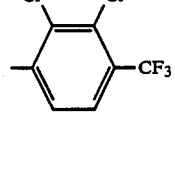 | m.p.: 122–127° C. |

TABLE 1-continued

| Ex. No. | R¹ | R² | R³ | Ar | Physical properties |
|---|---|---|---|---|---|
| 50 | NO₂ | H | −CO−CH(Cl)−CH₃ | 2,3-difluoro-5-chloro-6-CF₃-phenyl | m.p.: 105–197° C. |
| 51 | NO₂ | H | −CO−CH(Cl)−CH₃ | 2,3-dichloro-6-CF₃-phenyl | m.p.: 120–122° C. |
| 52 | H | H | −CO−CH(CH₃)−OC₂H₅ | 2-chloro-3-fluoro-5-chloro-6-CF₃-phenyl | ¹H-NMR* 6.7(d) |
| 53 | H | H | −CO−CH(CH₃)−OC₂H₅ | 2-chloro-3-fluoro-6-CF₃-phenyl | m.p.: 68–71° C. |
| 54 | H | H | −CO−CH(CH₃)−OC₂H₅ | 2-chloro-5-fluoro-6-CF₃-phenyl | ¹H-NMR* 6.7(t) |
| 55 | H | H | −CO−CH(CH₃)−OC₂H₅ | 2,3-dichloro-6-CF₃-phenyl | m.p.: 94–96° C. |
| 56 | NO₂ | H | −CO−CH(CH₃)−OC₂H₅ | 2-chloro-3-fluoro-6-CF₃-phenyl | m.p.: 101–103° C. |
| 57 | NO₂ | H | −CO−CH(CH₃)−OC₂H₅ | 2-chloro-5-fluoro-6-CF₃-phenyl | m.p.: 82–86° C. |
| 58 | NO₂ | H | −CO−CH(CH₃)−OC₂H₅ | 2,3-dichloro-6-CF₃-phenyl | m.p.: 124–126° C. |
| 59 | NO₂ | H | −CO−CH(CH₃)−OC₂H₅ | 2-chloro-3-fluoro-5-chloro-6-CF₃-phenyl | m.p.: 76–86° C. |

TABLE 1-continued

| Ex. No. | R¹ | R² | R³ | Ar | Physical properties |
|---|---|---|---|---|---|
| 60 | H | H | —CO—CH(CH₃)—OC₂H₅ | 3-Cl, 2-F, 4-CF₃, 6-F phenyl | m.p.: 84–88° C. |
| 61 | NO₂ | H | —CO—CH(CH₃)—OC₂H₅ | 2-F, 3-F, 4-CF₃, 6-Cl phenyl | m.p.: 93–96° C. |
| 62 | H | H | —CO—CH(CH₃)—OC₂H₅ | 2-F, 3-F, 4-CF₃, 6-Cl phenyl | ¹H-NMR* 7.78(d) |
| 63 | NO₂ | H | —CO—CH(CH₃)—OC₂H₅ | 3-Cl, 2-F, 4-CF₃, 6-F phenyl | ¹H-NMR* 8.33(s) |
| 64 | H | H | —CO—CH₂OCH₂CF₃ | 3-Cl, 2-F, 4-CF₃, 6-Cl phenyl | m.p.: 96–102° C. |
| 65 | NO₂ | H | —CO—CH₂CH₂Cl | 3-Cl, 4-CF₃, 6-F phenyl | m.p.: 93–96° C. |
| 66 | NO₂ | H | —CO—CH₂CH₂Cl | 3-Cl, 2-F, 4-CF₃, 6-Cl phenyl | m.p.: 118–124° C. |
| 67 | NO₂ | H | —CO—CH₂CH₂Cl | 3-Cl, 2-F, 4-CF₃ phenyl | oil |
| 68 | NO₂ | H | —CO—CH₂CH₂Cl | 2-F, 3-F, 4-CF₃, 6-Cl phenyl | m.p.: 138–141° C. |

TABLE 1-continued

| Ex. No. | R¹ | R² | R³ | Ar | Physical properties |
|---|---|---|---|---|---|
| 69 | NO₂ | H | —CO—CH₂CH₂Cl | 2,3-Cl₂-4-CF₃-phenyl | m.p.: 106°–109° C. |
| 70 | NO₂ | H | —CO—CH₂CH₂Cl | 2-Cl-3-F-4-CF₃-6-F-phenyl | oil |
| 71 | NO₂ | H | —C(O)—(CH₂)₂—OCH₃ | 2-F-4-CF₃-6-Cl-phenyl | m.p. 103–106° C. |
| 72 | NO₂ | H | —C(O)—(CH₂)₂—OCH₃ | 2-Cl-3-F-4-CF₃-6-Cl-phenyl | m.p. 80–85° C. |
| 73 | NO₂ | H | —C(O)—(CH₂)₂—OCH₃ | 2-Cl-3-F-4-CF₃-phenyl | m.p. 122–126° C. |
| 74 | NO₂ | H | —C(O)—(CH₂)₂—OCH₃ | 2-F-3-F-4-CF₃-6-Cl-phenyl | ¹H-NMR*: 8.34 |
| 75 | NO₂ | H | —C(O)—(CH₂)₂OCH₃ | 2,3-Cl₂-4-CF₃-phenyl | m.p. 125–128° C. |
| 76 | NO₂ | H | —C(O)—CH(Cl)—CH₃ | 2-Cl-3-F-4-CF₃-6-F-phenyl | m.p. 93–98° C. |
| 77 | NO₂ | H | —C(O)—CH(Cl)—C₂H₅ | 2-F-4-CF₃-6-Cl-phenyl | ¹H-NMR*: 8.37 |

TABLE 1-continued

| Ex. No. | R¹ | R² | R³ | Ar | Physical properties |
|---|---|---|---|---|---|
| 78 | $NO_2$ | H | -C(=O)-CHCl-$C_2H_5$ | 3,5-Cl₂-2-F-4-$CF_3$-phenyl | m.p. 78–87° C. |
| 79 | $NO_2$ | H | -C(=O)-CHCl-$C_2H_5$ | 2-Cl-3,6-F₂-4-$CF_3$-phenyl | m.p. 100–104° C. |
| 80 | $NO_2$ | H | -C(=O)-CHCl-$C_2H_5$ | 5-Cl-2,3-F₂-4-$CF_3$-phenyl | m.p. 93–99° C. |

*The ¹H-NMR spectra were recorded in deuterochloroform (CDCl₃) using tetramethylsilane (TMS) as internal standard. The data represent the chemical shift as δ-value in ppm.

Preparation of the starting compounds:

EXAMPLE II-1:

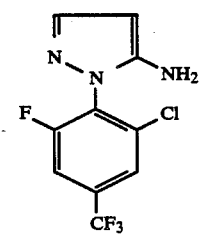

250 g (0.71 mol) of 5-amino-4-ethoxycarbonyl-1-(2-chloro-6-fluoro-4-trifluoromethylphenyl)-pyrazole are heated in 650 ml of 50% strength aqueous sulphuric acid at 120° C. for 2 hours, during which the volatile constituents distil off. The mixture is heated at 115° C. to 120° C. for a further 5 hours and then cooled, 3 l of ice-water are added, the pH is adjusted to 8 to 9 using aqueous sodium hydroxide solution, and the precipitate formed is filtered off, washed with water and dried in vacuo at 50° C. 163 g (82% of theory) of 5-amino-1-(2-chloro-6-fluoro-4-trifluoromethylphenyl)-pyrazole of melting point 87°–90° C. are obtained.

In a corresponding manner, the following 1-aryl-pyrazoles of the general formula (II)

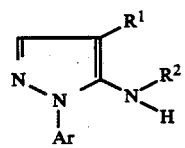

are obtained:

TABLE 2

| Ex. No. | R¹ | R² | Ar | Melting point °C. |
|---|---|---|---|---|
| II-2 | H | H | 3,5-Cl₂-2-F-4-$CF_3$-phenyl | 69–79 |
| II-3 | H | H | 3-Cl-2-F-4-$CF_3$-phenyl | 112–114 |
| II-4 | H | H | 2,3-Cl₂-4-$CF_3$-phenyl | 139–140 |
| II-5 | H | H | 2,3,5-F₃-4-$CF_3$-phenyl | 116–117 |
| II-6 | H | H | 5-Cl-2-F-4-$CF_3$-phenyl | 62–64 |

TABLE 2-continued

| Ex. No. | R¹ | R² | Ar | Melting point °C. |
|---|---|---|---|---|
| II-7 | H | H | (2-Cl, 3-F, 4-CF₃, 6-F phenyl) | 93–97 |
| II-8 | H | H | (2-F, 4-CF₃, 6-F phenyl) | 95–97 |
| II-9 | H | H | (2-F, 3-F, 4-CF₃, 5-Cl phenyl) | 85–89 |

EXAMPLE XIV-1:

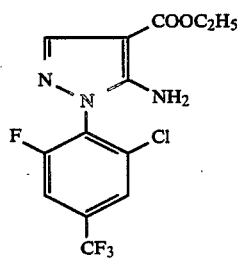

200 g (0.88 mol) of 2-chloro-6-fluoro-4-trifluoromethylphenylhydrazine and 151 g (0.88 mol) of ethyl ethoxymethylenecyanoacetate in 400 ml of ethanol are heated to the reflux temperature for 30 hours, the mixture is then concentrated to approximately half of the volume and cooled and the precipitate thus obtained is filtered off, washed with a little cold ethanol and dried. 250 g (81% of theory) of ethyl 5-amino-1-(2-chloro-6-fluoro-4-trifluoromethylphenyl)-pyrazol-4-yl carboxylate of melting point 147°–149° C. are obtained.

In a corresponding manner and according to the general instructions for the preparation, the following 1-arylpyrazole-4-carboxylates of the general formula (XIV)

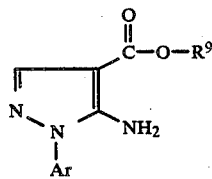 (XIV)

are obtained:

TABLE 3

| Ex. No. | R⁹ | Ar | Physical properties |
|---|---|---|---|
| XIV-2 | C₂H₅ | (2-Cl, 3-F, 4-CF₃, 6-Cl phenyl) | m.p.: 70–74° C. |
| XIV-3 | C₂H₅ | (2-Cl, 3-F, 4-CF₃ phenyl) | m.p.: 119–126° C. |
| XIV-4 | C₂H₅ | (2-Cl, 3-Cl, 4-CF₃ phenyl) | m.p.: 174–175° C. |
| XIV-5 | C₂H₅ | (2-F, 4-CF₃, 6-F phenyl) | m.p.: 132–133° C. |
| XIV-6 | C₂H₅ | (2-F, 4-CF₃, 5-Cl phenyl) | m.p.: 139° C. |
| XIV-7 | C₂H₅ | (2-F, 3-F, 4-CF₃, 6-F phenyl) | ¹H-MNR* 7.87 |
| XIV-8 | C₂H₅ | (2-Cl, 3-F, 4-CF₃, 6-F phenyl) | m.p.: 171–175° C. |
| XIV-9 | C₂H₅ | (2-F, 3-F, 4-CF₃, 6-Cl phenyl) | m.p.: 88° C. |

EXAMPLE XII-1:

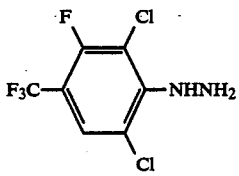

470 g (1.87 mol) of 3,5-dichloro-2,4-difluorobenzotrifluoride are initially introduced in 1000 ml of ethanol, 142 g (2.84 mol) of hydrazine hydrate are metered in, and the mixture is subsequently heated to reflux for 3 hours. The solvent is then removed by distillation under reduced pressure, and the residue is stirred into 1000 ml of cold water. After 30 minutes, the solid product is filtered off with suction and dried in a circulation dryer. 445 g (90% of theory) of 2,6-dichloro-3-fluoro-4-trifluoromethyl-phenylhydrazine of melting point 50° to 51° C. are obtained.

EXAMPLE XII-2:

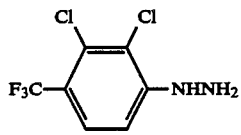

100 g (0.4 mol) of 2,3,4-trichlorobenzotrifluoride are initially introduced, 200 ml of pyridine and subsequently 100 g (2.0 mol) of hydrazine hydrate are added, and the mixture is then heated to the reflux temperature for 12 hours. 90% of the pyridine is then removed by distillation, and the residue remaining is stirred into 250 ml of water. The crystalline product is filtered off with suction, washed with some water and dried. 78 g (80% of theory) of 2,3-dichloro-4-trifluoromethyl-phenylhydrazine of melting point 79° to 80° C. are obtained.

In a corresponding manner and according to the general instructions for the preparation, the following aryl hydrazines of the formula (XII)

   (XII)

are obtained:

TABLE 4

| Ex. No. | Ar | Melting point °C. |
|---|---|---|
| XII-3 | 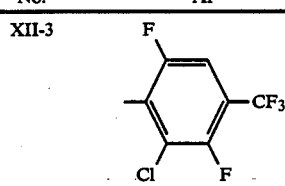 | 72-83 |
| XII-4 | 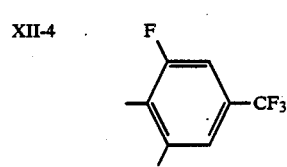 | 60-61 |
| XII-5 | Cl, F, CF₃ | 102-103 |
| XII-6 | F, F, CF₃, F | 60-62 |
| XII-7 | F, F, CF₃, F | 69-70 |
| XII-8 | F, F, CF₃, Cl | 80 |
| XII-9 | F, CF₃, Cl, F | 82-84 |
| XII-10 | F, CF₃, F | 41 |
| XII-11 | Cl, CF₃, F | 69-70 |

EXAMPLE XI-1/XI-2:

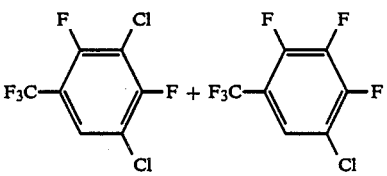

900 g (3.17 mol) of 2,3,4,5-tetrachlorobenzotrifluoride (cf., for example, European Patent Specification 150,587) are added to 800 g (13.8 mol) of potassium fluoride in 1800 ml of dry tetramethylenesulphone, and the mixture is heated at 200° C. for 10 hours. For working-up, the mixture is concentrated in vacuo and distilled.

Initially, 50 g (6.8% of theory) of 2,3,4-trifluoro-5-chloro-benzotrifluoride of boiling point b.p. 31°–38° C. at 10 mbar and of refraction index $n_D^{20} = 1.4130$ and, as a 2nd fraction, 490 g (61.6% of theory) of 2,4-difluoro-3,5-dichlorobenzotrifluoride of boiling point 57°–59° C. at 10 mbar and of refraction index $n_D^{20} = 1.4510$, are obtained.

EXAMPLE XI-3:

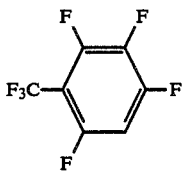

252.5 g (1 mol) of 3-chloro-2,4,5,6-tetrafluorobenzotrifluoride (cf., for example, Zh. obshch. Khim., 37, 1686–1687 [1967]) and 86 g (1.05 mol) of sodium acetate in 1000 ml of glacial acetic acid are hydrogenated in the presence of 10 g of palladium-on-activated charcoal (5% strength) at a hydrogen pressure of 30 to 50 bar and 120° C. to constant pressure. For working-up, the catalyst is removed from the cold reaction mixture by filtration, and the residue is distilled. 210 g (96% of theory) of 2,3,4,6-tetrafluorobenzotrifluoride of boiling point 105°–106° C. and of refraction index $n_D^{20} = 1.3770$ are obtained.

In a corresponding manner, the following aryl halides of the formula (XI)

Ar—Hal$^2$ (XI)

are obtained:

TABLE 5

| Ex. No. | Ar | Hal$^2$ | Boiling point/mbar Refraction index $n_D^{20}$ |
|---|---|---|---|
| XI-4 |  | F | b.p.: 45° C./760 $n_D^{20} = 1.4170$ |
| XI-5 | Cl, F, CF$_3$ | F | b.p.: 37° C./16 $n_D^{20} = 1.4268$ |
| XI-6 | F, CF$_3$, F | F | b.p.: 104° C./760 $n_D^{20} = 1.3862$ |
| XI-7 | F, CF$_3$, Cl | F | b.p.: 130–140° C./760 $n_D^{20} = 1.4250$ |

USE EXAMPLES:

In the following use examples, the compound mentioned below has been used as a comparison substance:

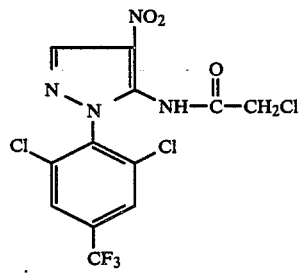

4-Nitro-5-chloroacetamido-1-(2,6-dichloro-4-trifluoromethylphenyl)-pyrazole (disclosed in DE-OS (German Published Specification) 3,402,308/Example No. 20).

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, the compounds according to the following preparation examples: 3, 4, 6, 8, 11, 13, 24, 26, 27, 29, 30, 31, 33, 34, 40, 43, 45 and 46, for example, have a clearly superior activity, while having a comparable crop plant selectivity, as compared with the comparison substance (A).

EXAMPLE B

Post-emergence test

Solvent: 5 parts by weight of acetone

Emulsifier: 1 part of weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is chosen so that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, the compounds according to the following preparation examples: 3, 6, 13, 24, 25, 26, 28, 29, 30, 31, 32, 33, 34, 40, 43, 44, 45, 46 and 47, for example, have a clearly superior activity, as compared with the comparison substance (A).

EXAMPLE C

Defoliation and desiccation of the leaves of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings:
0 denotes no desiccation of the leaves, no shedding of leaves
+ denotes slight desiccation of the leaves, slight shedding of leaves
++ denotes severe desiccation of the leaves, severe shedding of leaves
+++ denotes very severe desiccation of the leaves, very severe shedding of leaves In this test, the compounds according to the preparation examples 1, 3, 6, 7, 8, 10, 11, 12, 19, 21, 24, 25, 26, 27, 28, 29, 30, 31, 32, 33, 34, 43, 44, 45 and 46, have a distinct activity, as compared with the untreated control.

It will be appreciated that the instant specification and claims are set forth by way of illustration and not limitation, and that various modifications and changes may be made without departing from the spirit and scope of the present invention.

What is claimed is:

1. A 1-arylpyrazole of the formula

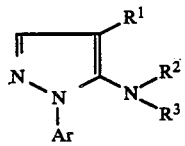

in which
$R^1$ stands for nitro,
$R^2$ stands for hydrogen,
$R^3$ stands for

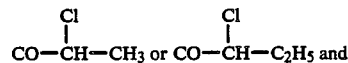

and $R^4$ stands for

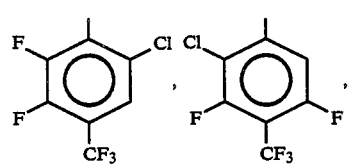

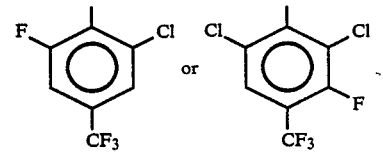

2. A 1-arylpyrazole according to claim 1 having a formula selected from the group consisting of

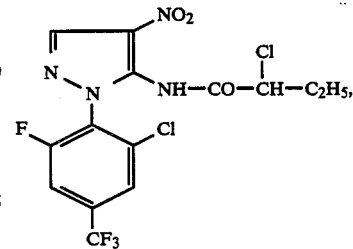

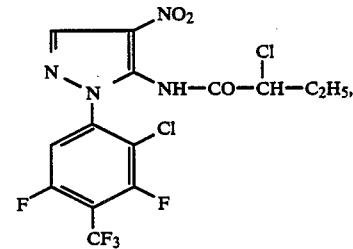

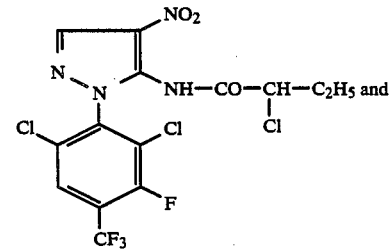

-continued

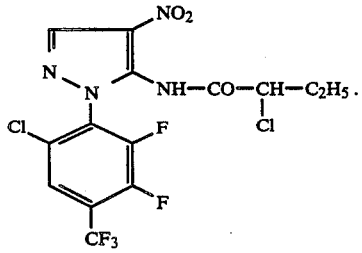

3. A 1-arylpyrazole according to claim 1 of the formula

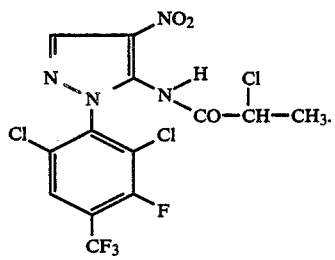

4. A 1-arylpyrazole according to claim 1 of the formula

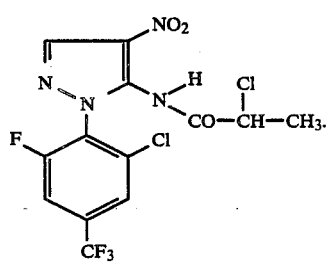

5. A 1-arylpyrazole according to claim 1 of the formula

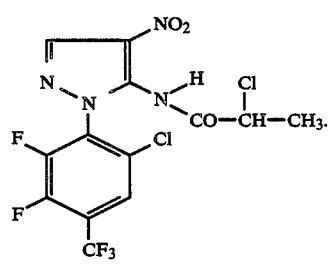

6. A 1-arylpyrazole according to claim 1 of the formula

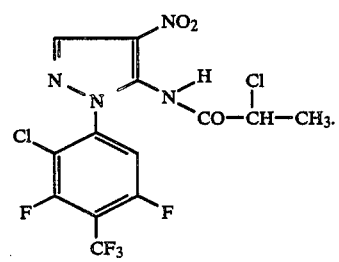

7. A herbicidal composition comprising a herbicidally effective amount of a 1-arylpyrazole according to claim 1 in admixture with a diluent.

8. A herbicidal composition according to claim 7, wherein the 1-arylpyrazole is selected from the group consisting of

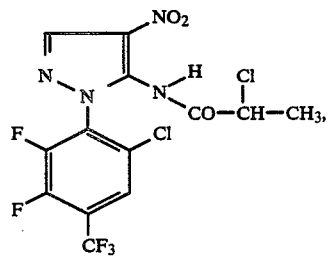

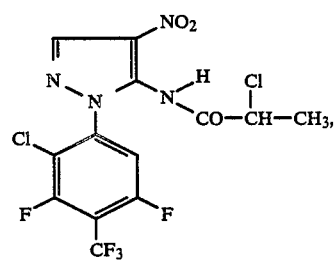

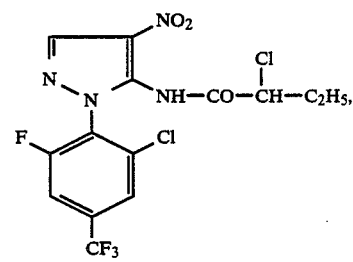

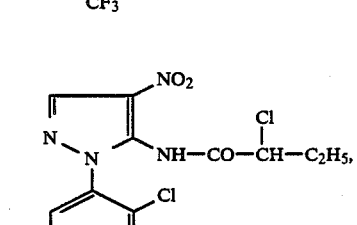

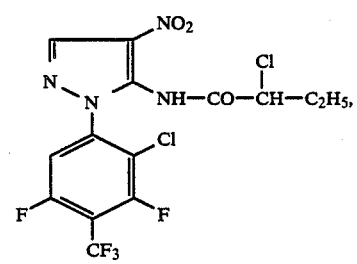

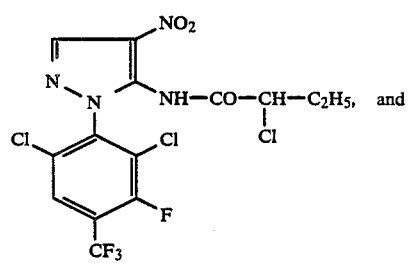

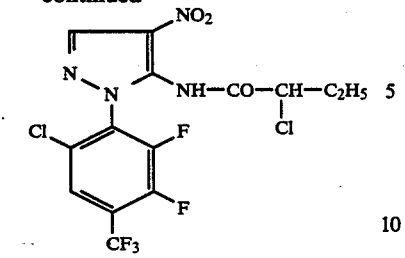

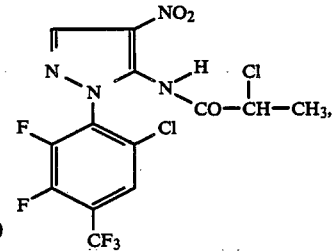

9. A herbicidal composition according to claim 7, wherein the 1-arylpyrazole is selected from the group consisting of

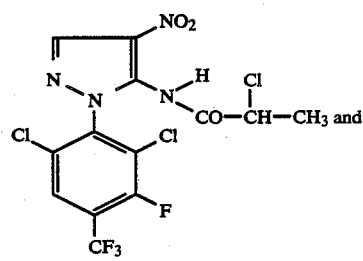

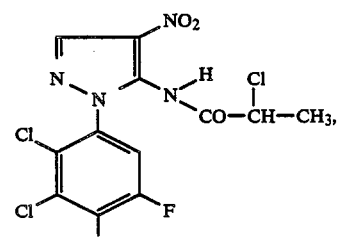

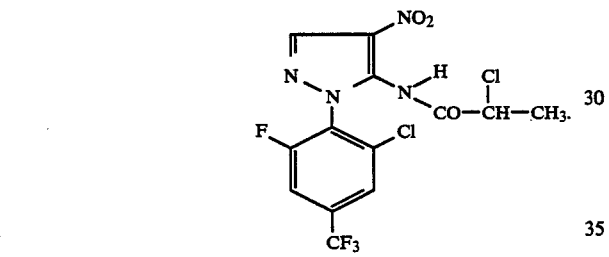

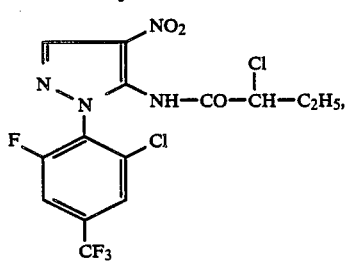

10. A plant growth-regulant composition comprising a plant growth-regulant effective amount of a 1-arylpyrazole according to claim 1 in admixture with a diluent.

11. A plant growth-regulant composition according to claim 10, wherein the 1-arylpyrazole is selected from the group consisting of

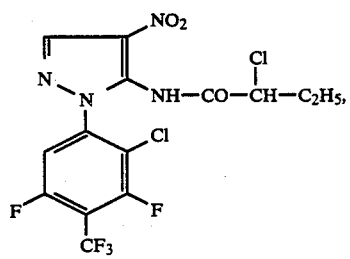

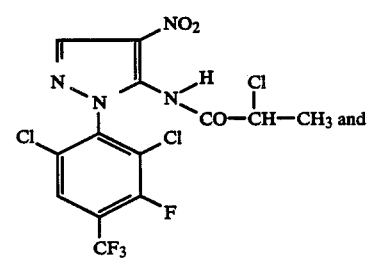

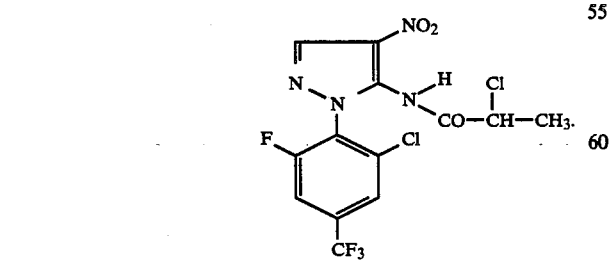

12. A plant growth-regulant composition according to claim 10, wherein the 1-arylpyrazole is selected from the group consisting of

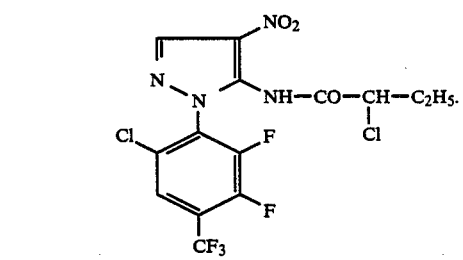

13. A method of combating unwanted vegetation which comprises applying to such vegetation or to a locus from which it is desired to exclude such vegetation a herbicidally effective amount of a 1-arylpyrazole according to claim 1.

14. A method of regulating plant growth which comprises applying to plants a plant growth-regulating effective amount of a 1-arylpyrazole according to claim 1.

* * * * *

UNITED STATES PATENT AND TRADEMARK OFFICE
CERTIFICATE OF CORRECTION

PATENT NO. : 4,936,892

DATED : June 26, 1990

INVENTOR(S) : Gehring et al.

It is certified that error appears in the above-identified patent and that said Letters Patent is hereby corrected as shown below:

Col. 74 claim 12 line 19   Delete " 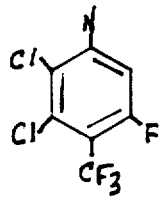 " and substitute -- 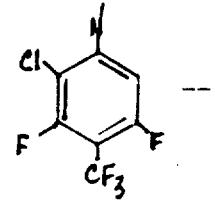 --

Signed and Sealed this

Twenty-eighth Day of April, 1992

Attest:

HARRY F. MANBECK, JR.

Attesting Officer  Commissioner of Patents and Trademarks